United States Patent
Doxey et al.

(10) Patent No.: US 10,265,334 B2
(45) Date of Patent: *Apr. 23, 2019

(54) ANHYDROUS COMPOSITIONS

(71) Applicant: Novan, Inc., Durham, NC (US)

(72) Inventors: Ryan Doxey, Raleigh, NC (US); Nathan Stasko, Durham, NC (US)

(73) Assignee: Novan, Inc., Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/887,648

(22) Filed: Oct. 20, 2015

(65) Prior Publication Data

US 2016/0038390 A1 Feb. 11, 2016

Related U.S. Application Data

(63) Continuation of application No. 14/134,737, filed on Dec. 19, 2013, now Pat. No. 9,289,442, which is a continuation of application No. PCT/US2012/045384, filed on Jul. 3, 2012.

(60) Provisional application No. 61/610,137, filed on Mar. 13, 2012, provisional application No. 61/504,628, filed on Jul. 5, 2011.

(51) Int. Cl.
| | |
|---|---|
| *A61K 8/34* | (2006.01) |
| *A61K 8/40* | (2006.01) |
| *A61K 9/00* | (2006.01) |
| *A61K 9/14* | (2006.01) |
| *A61K 47/34* | (2017.01) |
| *A61K 47/38* | (2006.01) |
| *A61Q 19/00* | (2006.01) |
| *A61K 8/58* | (2006.01) |
| *A61K 8/73* | (2006.01) |
| *A61K 47/10* | (2017.01) |
| *A61K 47/20* | (2006.01) |
| *A61K 8/368* | (2006.01) |
| *A61K 31/695* | (2006.01) |

(52) U.S. Cl.
CPC .............. *A61K 31/695* (2013.01); *A61K 8/34* (2013.01); *A61K 8/345* (2013.01); *A61K 8/368* (2013.01); *A61K 8/40* (2013.01); *A61K 8/585* (2013.01); *A61K 8/731* (2013.01); *A61K 9/0014* (2013.01); *A61K 47/10* (2013.01); *A61K 47/20* (2013.01); *A61K 47/34* (2013.01); *A61K 47/38* (2013.01); *A61Q 19/00* (2013.01); *A61K 9/143* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 3,754,368 A | 8/1973 | Moore et al. | |
| 4,182,827 A | 1/1980 | Jones et al. | |
| 4,829,092 A | 5/1989 | Nelson et al. | |
| 4,917,886 A | 4/1990 | Asche et al. | |
| 5,405,919 A | 4/1995 | Keefer | |
| 5,519,020 A | 5/1996 | Smith et al. | |
| 5,691,423 A | 11/1997 | Smith et al. | |
| 5,770,645 A | 6/1998 | Stamler et al. | |
| 5,814,656 A | 9/1998 | Saavedra et al. | |
| 5,814,666 A | 9/1998 | Green et al. | |
| 5,840,759 A | 11/1998 | Mitchell et al. | |
| 5,910,316 A | 6/1999 | Keefer et al. | |
| 5,912,008 A * | 6/1999 | Horstmann | A61K 9/7053 424/448 |
| 5,958,427 A | 9/1999 | Salzman et al. | |
| 5,968,528 A | 10/1999 | Deckner et al. | |
| 6,103,266 A | 8/2000 | Tapolsky et al. | |
| 6,103,275 A | 8/2000 | Seitz et al. | |
| 6,110,453 A | 8/2000 | Keefer et al. | |
| 6,303,141 B1 | 10/2001 | Fischer et al. | |
| 6,319,913 B1 | 11/2001 | Mak et al. | |
| 6,382,526 B1 | 5/2002 | Reneker et al. | |
| 6,465,445 B1 | 10/2002 | Labrie | |
| 6,479,058 B1 | 11/2002 | McCadden | |
| 6,520,425 B1 | 2/2003 | Reneker | |
| 6,695,992 B2 | 2/2004 | Reneker | |
| 6,737,447 B1 | 5/2004 | Smith et al. | |
| 6,818,018 B1 | 11/2004 | Sawhney | |
| 6,861,064 B1 | 3/2005 | Laakso et al. | |
| 7,048,951 B1 | 5/2006 | Seitz et al. | |
| 7,704,518 B2 | 4/2010 | Tamarkin et al. | |
| 8,241,650 B2 | 8/2012 | Peters | |
| 8,343,945 B2 | 1/2013 | Tamarkin et al. | |
| 8,362,091 B2 | 1/2013 | Tamarkin et al. | |
| 8,399,005 B2 | 3/2013 | Schoenfisch et al. | |
| 8,486,374 B2 | 7/2013 | Tamarkin et al. | |
| 8,486,451 B2 | 7/2013 | Morris et al. | |
| 8,591,876 B2 | 11/2013 | Bauman et al. | |
| 8,617,100 B2 | 12/2013 | Eini et al. | |
| 8,636,982 B2 | 1/2014 | Tamarkin et al. | |
| 8,722,103 B2 | 5/2014 | Morris et al. | |
| 8,795,635 B2 | 8/2014 | Tamarkin et al. | |
| 8,795,693 B2 | 8/2014 | Tamarkin et al. | |
| 8,900,553 B2 | 12/2014 | Tamarkin et al. | |

(Continued)

FOREIGN PATENT DOCUMENTS

| | | |
|---|---|---|
| CA | 2 594 407 A1 | 8/2006 |
| EP | 1 300 424 A1 | 4/2003 |

(Continued)

OTHER PUBLICATIONS

Peyrot et al. English Machine Translation of WO2000/02593 [online] espacenet, 2016 [retrieved on Sep. 27, 2016]. Retrieved from the internet <espacenet.com>.*

(Continued)

*Primary Examiner* — Katherine Peebles
(74) *Attorney, Agent, or Firm* — Myers Bigel, P.A.

(57) ABSTRACT

Provided herein are anhydrous compositions that include at least one viscosity increasing agent, at least one organic solvent and at least one humectant. Such compositions may also include at least one active pharmaceutical ingredient (API) and/or at least one water repellant. Related compositions, methods and kits are also provided.

18 Claims, 9 Drawing Sheets

(56) References Cited

U.S. PATENT DOCUMENTS

| | | | |
|---|---|---|---|
| 9,101,662 B2 | 8/2015 | Tamarkin et al. | |
| 9,161,916 B2 | 10/2015 | Tamarkin et al. | |
| 9,265,725 B2 | 2/2016 | Tamarkin et al. | |
| 9,320,705 B2 | 4/2016 | Tamarkin et al. | |
| 9,526,738 B2 * | 12/2016 | Stasko | A61K 9/0014 |
| 9,757,397 B2 * | 9/2017 | Kougoulos | A61K 31/655 |
| 9,855,211 B2 * | 1/2018 | Doxey | A61K 9/0014 |
| 2002/0012816 A1 | 1/2002 | Shimizu et al. | |
| 2002/0013304 A1 | 1/2002 | Wilson et al. | |
| 2002/0028223 A1 | 3/2002 | Vatter et al. | |
| 2002/0082221 A1 | 6/2002 | Herrmann et al. | |
| 2002/0094985 A1 | 7/2002 | Herrmann et al. | |
| 2002/0122771 A1 | 9/2002 | Holland et al. | |
| 2002/0136750 A1 | 9/2002 | Benjamin et al. | |
| 2002/0155174 A1 | 10/2002 | Benjamin et al. | |
| 2003/0077243 A1 | 4/2003 | Fitzhugh | |
| 2003/0159702 A1 | 8/2003 | Lindell et al. | |
| 2003/0175328 A1 | 9/2003 | Shefer et al. | |
| 2003/0205234 A1 | 11/2003 | Bardach et al. | |
| 2003/0235605 A1 | 12/2003 | Lelah et al. | |
| 2004/0009238 A1 | 1/2004 | Miller et al. | |
| 2004/0043068 A1 | 3/2004 | Tedeschi et al. | |
| 2004/0068005 A1 | 4/2004 | Szilvassy et al. | |
| 2004/0171589 A1 | 9/2004 | Herrmann et al. | |
| 2004/0202684 A1 | 10/2004 | Djerassi | |
| 2004/0220260 A1 | 11/2004 | Cals-Grierson | |
| 2004/0265244 A1 | 12/2004 | Rosen | |
| 2005/0038473 A1 | 2/2005 | Tamarkin et al. | |
| 2005/0232869 A1 | 10/2005 | Tamarkin et al. | |
| 2005/0271596 A1 | 12/2005 | Friedman et al. | |
| 2006/0160897 A1 | 7/2006 | Pelicci et al. | |
| 2006/0173076 A1 | 8/2006 | Vishnupad et al. | |
| 2006/0269620 A1 | 11/2006 | Morris et al. | |
| 2006/0275218 A1 | 12/2006 | Tamarkin et al. | |
| 2007/0166255 A1 | 7/2007 | Gupta | |
| 2007/0292359 A1 | 12/2007 | Friedman et al. | |
| 2007/0292461 A1 | 12/2007 | Tamarkin et al. | |
| 2008/0031907 A1 | 2/2008 | Tamarkin et al. | |
| 2008/0044444 A1 | 2/2008 | Tamarkin et al. | |
| 2008/0063607 A1 | 3/2008 | Tamarkin et al. | |
| 2008/0069779 A1 | 3/2008 | Tamarkin et al. | |
| 2008/0071206 A1 | 3/2008 | Peters | |
| 2008/0138296 A1 | 6/2008 | Tamarkin et al. | |
| 2008/0152596 A1 | 6/2008 | Friedman et al. | |
| 2008/0166303 A1 | 7/2008 | Tamarkin et al. | |
| 2008/0206155 A1 | 8/2008 | Tamarkin et al. | |
| 2008/0206159 A1 | 8/2008 | Tamarkin et al. | |
| 2008/0206161 A1 | 8/2008 | Tamarkin et al. | |
| 2008/0253973 A1 | 10/2008 | Tamarkin et al. | |
| 2008/0260655 A1 | 10/2008 | Tamarkin et al. | |
| 2008/0292560 A1 | 11/2008 | Tamarkin et al. | |
| 2008/0299220 A1 | 12/2008 | Tamarkin et al. | |
| 2008/0311163 A1 | 12/2008 | Peters | |
| 2008/0317679 A1 | 12/2008 | Tamarkin et al. | |
| 2009/0041680 A1 | 2/2009 | Tamarkin et al. | |
| 2009/0068118 A1 | 3/2009 | Eini et al. | |
| 2009/0068248 A1 | 3/2009 | Waterhouse et al. | |
| 2009/0130029 A1 | 5/2009 | Tamarkin et al. | |
| 2009/0175799 A1 | 7/2009 | Tamarkin et al. | |
| 2009/0214618 A1 | 8/2009 | Schoenfisch et al. | |
| 2009/0226380 A1 | 9/2009 | Clark et al. | |
| 2009/0297634 A1 | 12/2009 | Friedman et al. | |
| 2010/0098733 A1 | 4/2010 | Stasko | |
| 2010/0221195 A1 | 9/2010 | Tamarkin et al. | |
| 2010/0266510 A1 | 10/2010 | Tamarkin et al. | |
| 2010/0286285 A1 | 11/2010 | Barthez et al. | |
| 2010/0310476 A1 | 12/2010 | Tamarkin et al. | |
| 2010/0331968 A1 | 12/2010 | Morris et al. | |
| 2011/0027369 A1 | 2/2011 | Franke | |
| 2011/0045037 A1 | 2/2011 | Tamarkin et al. | |
| 2011/0052650 A1 | 3/2011 | Morris et al. | |
| 2011/0082167 A1 | 4/2011 | Pisak et al. | |
| 2011/0086234 A1 | 4/2011 | Stasko et al. | |
| 2011/0097279 A1 | 4/2011 | Tamarkin et al. | |
| 2011/0212033 A1 | 9/2011 | Tamarkin et al. | |
| 2012/0114547 A1 | 5/2012 | Smith | |
| 2012/0134951 A1 | 5/2012 | Stasko et al. | |
| 2012/0136323 A1 | 5/2012 | Stasko et al. | |
| 2012/0141384 A1 | 6/2012 | Tamarkin et al. | |
| 2012/0156163 A1 | 6/2012 | Bauman et al. | |
| 2012/0237453 A1 | 9/2012 | Tamarkin et al. | |
| 2013/0059017 A1 | 3/2013 | Perricone et al. | |
| 2013/0109756 A1 | 5/2013 | Huber et al. | |
| 2013/0164225 A1 | 6/2013 | Tamarkin et al. | |
| 2013/0189191 A1 | 7/2013 | Tamarkin et al. | |
| 2013/0189193 A1 | 7/2013 | Tamarkin et al. | |
| 2013/0189195 A1 | 7/2013 | Tamarkin et al. | |
| 2013/0310533 A1 | 11/2013 | Bao et al. | |
| 2013/0344334 A1 | 12/2013 | Schoenfisch et al. | |
| 2014/0017121 A1 | 1/2014 | Schoenfisch et al. | |
| 2014/0057001 A1 | 2/2014 | Bauman et al. | |
| 2014/0058124 A1 | 2/2014 | Schoenfisch et al. | |
| 2014/0065200 A1 | 3/2014 | Schoenfisch et al. | |
| 2014/0107071 A1 | 4/2014 | Kougoulos et al. | |
| 2014/0134321 A1 | 5/2014 | Stasko et al. | |
| 2014/0171395 A1 | 6/2014 | Schoenfisch et al. | |
| 2014/0193502 A1 | 7/2014 | Tamarkin et al. | |
| 2014/0242023 A1 | 8/2014 | Doxey et al. | |
| 2014/0248219 A1 | 9/2014 | Tamarkin et al. | |
| 2014/0255318 A1 | 9/2014 | Stasko et al. | |
| 2014/0271494 A1 | 9/2014 | Tamarkin et al. | |
| 2014/0369949 A1 | 12/2014 | Peters | |
| 2015/0017103 A1 | 1/2015 | Tamarkin et al. | |
| 2015/0024052 A1 | 1/2015 | Doxey | |
| 2015/0025060 A1 | 1/2015 | Tamarkin et al. | |
| 2015/0111973 A1 | 4/2015 | Bauman et al. | |
| 2015/0118164 A1 | 4/2015 | Tamarkin et al. | |
| 2015/0141606 A1 | 5/2015 | Bao et al. | |
| 2015/0182543 A1 | 7/2015 | Schoenfisch et al. | |
| 2015/0225488 A1 | 8/2015 | Schoenfisch et al. | |

FOREIGN PATENT DOCUMENTS

| | | |
|---|---|---|
| EP | 1 707 224 A1 | 10/2006 |
| EP | 1 861 130 B1 | 9/2008 |
| EP | 1 871 433 B1 | 4/2009 |
| EP | 1 846 058 B1 | 7/2009 |
| EP | 2 119 459 A1 | 11/2009 |
| EP | 2 142 179 A1 | 1/2010 |
| EP | 2 142 181 A1 | 1/2010 |
| EP | 1 917 005 B1 | 9/2010 |
| GB | 2 354 441 | 3/2001 |
| JP | 2003-183150 | 7/2003 |
| JP | 2006-248942 | 9/2006 |
| WO | WO 93/10754 A1 | 6/1993 |
| WO | WO 96/13164 A1 | 5/1996 |
| WO | WO 96/15797 A1 | 5/1996 |
| WO | WO 98/05689 A1 | 2/1998 |
| WO | WO 99/63974 A2 | 12/1999 |
| WO | WO 2000/02593 * | 1/2000 |
| WO | WO 00/33877 A1 | 6/2000 |
| WO | WO 00/49993 A2 | 8/2000 |
| WO | WO 01/21148 A1 | 3/2001 |
| WO | WO 01/26702 A2 | 4/2001 |
| WO | WO 01/85013 A2 | 11/2001 |
| WO | WO 02/020026 A2 | 3/2002 |
| WO | WO 02/056864 A2 | 7/2002 |
| WO | WO 03/013489 A1 | 2/2003 |
| WO | WO 03/072039 A2 | 9/2003 |
| WO | WO 03/078437 A1 | 9/2003 |
| WO | WO 03/086282 A2 | 10/2003 |
| WO | WO 03/092763 A1 | 11/2003 |
| WO | WO 2004/012659 A2 | 2/2004 |
| WO | WO 2004/012874 A1 | 2/2004 |
| WO | WO 2004/098538 A2 | 11/2004 |
| WO | WO 2005/003032 A1 | 1/2005 |
| WO | WO 2005/004984 A1 | 1/2005 |
| WO | WO 2005/011575 A2 | 2/2005 |
| WO | WO 2005/037339 A1 | 4/2005 |
| WO | WO 2005/046661 A2 | 5/2005 |
| WO | WO 2006/084910 A2 | 8/2006 |
| WO | WO 2006/084912 A1 | 8/2006 |
| WO | WO 2006/100154 A1 | 9/2006 |
| WO | WO 2006/128121 A2 | 11/2006 |

(56) References Cited

FOREIGN PATENT DOCUMENTS

| | | |
|---|---|---|
| WO | WO 2006/138035 A1 | 12/2006 |
| WO | WO 2007/007208 A2 | 1/2007 |
| WO | WO 2007/023005 A1 | 3/2007 |
| WO | WO 2007/023396 A2 | 3/2007 |
| WO | WO 2007/054818 A2 | 5/2007 |
| WO | WO 2008/032212 A2 | 3/2008 |
| WO | WO 2008/038140 A2 | 4/2008 |
| WO | WO 2008/038147 A2 | 4/2008 |
| WO | WO 2008/110872 A2 | 9/2008 |
| WO | WO 2008/116497 A1 | 10/2008 |
| WO | WO 2008/116925 A1 | 10/2008 |
| WO | WO 2008/152444 A2 | 12/2008 |
| WO | WO 2009/007785 A2 | 1/2009 |
| WO | WO 2009/049208 A1 | 4/2009 |
| WO | WO 2009/056991 A2 | 5/2009 |
| WO | WO 2009/067095 A1 | 5/2009 |
| WO | WO 2009/072007 A2 | 6/2009 |
| WO | WO 2009/087578 A2 | 7/2009 |
| WO | WO 2009/090495 A2 | 7/2009 |
| WO | WO 2009/098595 A2 | 8/2009 |
| WO | WO 2009/131931 A1 | 10/2009 |
| WO | WO 2011/005846 A1 | 1/2011 |
| WO | WO 2011/022652 A1 | 2/2011 |
| WO | WO 2011/022680 A2 | 2/2011 |
| WO | WO 2011/061519 A2 | 5/2011 |
| WO | WO 2012/100174 A1 | 7/2012 |
| WO | WO 2012/153331 A2 | 11/2012 |
| WO | WO 2013/006608 A1 | 1/2013 |
| WO | WO 2013/006613 A1 | 1/2013 |
| WO | WO 2013/138073 A1 | 9/2013 |
| WO | WO 2013/138075 A1 | 9/2013 |
| WO | WO 2015/021382 A2 | 2/2015 |

OTHER PUBLICATIONS

U.S. Appl. No. 14/133,973, filed Dec. 19, 2013, Kougoulos et al.
Amadeu et al. "Nitric Oxide Donor Improves Healing if Applied on Inflammatory and Proliferative Phase" *Journal of Surgical Research* 149:84-93 (2008).
Bohl Masters et al. "Effects of nitric oxide releasing poly(vinyl alcohol) hydrogel dressings on dermal wound healing in diabetic mice" *Wound Repair and Regeneration* 10(5):286-294 (2002).
Extended European Search Report corresponding to European Patent Application No. 12807939.9 (9 pages) (dated Dec. 17, 2014).
Hetrick et al. "Anti-biofilm efficacy of nitric oxide-releasing silica nanoparticles" *Biomaterials* 30:2782-2789 (2009), Feb. 23, 2009.
International Preliminary Report on Patentability corresponding to International Patent Application No. PCT/US2012/045384 (8 pages) (dated Jan. 7, 2014).
International Preliminary Report on Patentability corresponding to International Patent Application No. PCT/US2012/045390 (8 pages) (dated Jan. 7, 2014).
International Search Report and the Written Opinion of the International Searching Authority corresponding to International Patent Application No. PCT/US2012/045384 (12 pages) (dated Nov. 5, 2012).
International Search Report and the Written Opinion of the International Searching Authority corresponding to International Patent Application No. PCT/US2012/045390 (12 pages) (dated Dec. 11, 2012).
Product Data Sheet "LR-2.ST." *IKA-Werke Staufen, Germany* (2 pages) 2007.
Office Action corresponding to Japanese Patent Application No. 2014-519252 (7 pages) (dated Mar. 15, 2016).
European Patent Office Communication pursuant to Article 94(3) EPC corresponding to European Patent Application No. 12 807 939.9 (8 pages) (dated Feb. 18, 2016).
Sangster, James "Octanol-Water Partition Coefficients of Simple Organic Compounds" *Journal of Physical and Chemical Reference Data* 18(3):1111-1227 (1989).
U.S. Appl. No. 14/191,958, filed Feb. 27, 2014, Doxey et al.
Al-Sa'Doni et al. "S-Nitrosothiols: a class of nitric oxide-donor drugs" *Clinical Science* 98:507-520 (2000).
Boykin et al. "HBO Mediates Increased Nitric Oxide Production Associated With Wound Healing" *Wound Repaid and Regeneration* 12(2):A15 (Abstract 054) (2004).
Hrabie et al. "Chemistry of the Nitric Oxide-Releasing Diazeniumdiolate ("Nitrosohydroxylamine") Functional Group and Its Oxygen-Substituted Derivatives" *Chemical Reviews* 102:1135-1154 (2002).
Pulfer et al. "Incorporation of nitric oxide-releasing crosslinked polyethyleneimine microspheres into vascular grafts" *Journal of Biomedical Materials Research* 37:182-189 (1997).
Smith et al. "Transdermal delivery of nitric oxide from diazeniumdiolates" *Journal of Controlled Release* 51:153-159 (1998).
Wang et al. "Nitric Oxide Donors: Chemical Activities and Biological Applications" *Chemical Reviews* 102:1091-1134 (2002).
U.S. Appl. No. 14/771,138, filed Aug. 27, 2015, Doxey et al.
Office Action corresponding to Japanese Patent Application No. 2014-519252 (7 pages) (dated Sep. 26, 2017).
Office Action corresponding to related Japanese Patent Application No. 2017-088528 (8 pages) (Jan. 19, 2018).

\* cited by examiner

ANHYDROUS COMPOSITIONS

RELATED APPLICATION DATA

This application claims the benefit of U.S. Provisional Patent Application Ser. No. 61/504,628, filed Jul. 5, 2011, and U.S. Provisional Patent Application Ser. No. 61/610,137, filed Mar. 13, 2012, the disclosure of each of which are incorporated herein by reference in their entirety.

FIELD OF THE INVENTION

The present invention is directed to pharmaceutical compositions. In particular, the present invention is directed to anhydrous topical pharmaceutical compositions.

BACKGROUND OF THE INVENTION

Acne vulgaris is the most common skin disease in the United States. It is estimated that 40 to 50 million Americans have acne, including 80% of people between the ages of 11 and 30. The annual direct costs associated with the treatment of acne exceeded $2.8 billion in 2007, with the majority of those costs attributable to prescription drugs. In addition, acne causes both physical and psychological effects, including permanent scarring, anxiety, depression, and poor self-esteem. Even in cases of mild acne, the social stigma associated with the disease frequently results in significant emotional distress and other psychological issues. Due to its social impact, frequency of recurrence of relapse, and necessary maintenance over a prolonged course of therapy, the American Academy of Dermatologists have recommend that acne vulgaris be re-classified and investigated as a chronic disease.

Acne vulgaris results from the complex interplay of four major pathogenic factors: 1) overproduction of sebum by the sebaceous gland; 2) abnormal keratinization in the follicle; 3) colonization of the hair follicles by the anaerobic, lipophilic bacterium *Propionibacterium acnes*, or *P. acnes*; and 4) release of inflammatory mediators into the skin. All acne lesions begin when the combination of excess sebum and abnormal epithelial desquamation clog up a follicle, forming a microscopic lesion known as a microcomedo. The anaerobic, lipid-rich environment of the microcomedo provides an ideal location for *P. acnes* proliferation. Each microcomedo may progress to form a non-inflammatory open or closed comedone (commonly referred to as a "blackhead" or "whitehead," respectively), or an inflammatory lesion that may be further categorized as a papule, pustule, nodule, or cyst.

The complexity of the disease may require multiple treatments that may span oral and topical antimicrobials, oral and topical retinoids, oral contraceptives and other prescription skin cleansers. The most effective therapies for acne are those that may safely address more than one of the major causes of acne pathogenesis.

Antibiotics were the first successful acne treatment due to their antimicrobial and anti-inflammatory properties. Both topical and systemic antibiotics have been very successful, but the protracted treatment periods required have led to the development of resistance of *P. acnes* and in other non-targeted (and potentially pathogenic) commensal organisms. Combining antibiotics with topical retinoids targets three of the four major pathogenic factors associated with acne (all but sebum production). The oral retinoid isotretinoin (e.g., Accutane®) is the only drug-implicated to affect all four pathogenic factors associated with acne. However, the severity of its potential side effects (known teratogen and linked to depression, psychosis and suicide) has limited its use and led to numerous lawsuits.

While the problems associated with isotretinoin are the most severe, all of the current acne medications have some adverse effects. The majority of topical treatments lead to dryness, irritation and peeling of the skin, and oral antibiotics may cause gastrointestinal tract irritation, photosensitivity of skin, headache, dizziness, anemia, bone and joint pain, nausea and/or depression.

The most commonly prescribed drugs from acne are antibiotics, including benzoyl peroxide, clindamycin and erythromycin, either alone or in combination, and retinoids, including adapalene, tretinoin and tazarotene, either alone or in combination with an antibiotic. Treatments may include combination drugs or combination therapies. For example, a retinoid may be prescribed for application in the morning and an antibiotic for application in the evening. Each of these commonly prescribed drugs, however, has disadvantages that often reduce the effectiveness of the therapy.

For example, benzoyl peroxide may be the most effective topical medicine for acne and may result in a rapid reduction in *P. acnes*. It also does not induce drug resistance in the *P. acnes* and, when combined with other antibiotics, may reduce the rate at which drug resistance develops. However, benzoyl peroxide commonly results in irritation and dryness of the skin and bleaches fabric. Additionally, about 2% of patients have an allergic reaction to benzoyl peroxide.

Clindamycin and erythromycin as monotherapies may be limited in effectiveness because of the development of drug resistant strains of *P. acnes*. In fact, it is estimated that up to 75% of *P. acnes* is already resistant to these antibiotics. However, these products are available in a number of different bases and are typically non-irritating and non-staining.

Retinoids mainly target comedonal acne but may also reduce inflammatory lesions. Retinoids, however, are slow to produce visible results and may produce irritation, redness and peeling. In light of these limitations of retinoids, they are typically not used alone.

Combinations of these various drugs are also available. For example, clindamycin and benzoyl peroxide combination drugs are available as well as combinations of erythromycin and benzoyl peroxide, combinations of adapalene and benzoyl peroxide and combinations of clindamycin and tretinoin. These drugs may have improved efficacy over the individual drugs but also carry with them the limitations of their constituents. Furthermore, none of these combinations address all four of the causes of acne.

In addition to the limitations of the available drugs themselves, a number of additional factors may affect compliance with a treatment regime and, therefore, may reduce the regime's overall efficacy. These factors include the degree of irritation of the product, the time to noticeable results, the aesthetics of the product, the repeatability required, the effect on clothing and other items the product comes in contact with and the convenience of the packaging and storage of the product. If the product irritates the skin, the patient may discontinue use. If the product takes too long to provide visible results, the patient may get frustrated and stop treatment. If the product feels greasy, leaves a visible residue or is powdery and grating, the patient may be less likely to maintain the regime. If the product stains or bleaches clothes, bedding or other fabrics, the patient may discontinue its use. Finally, if the product is too difficult to use or store, the patient may be unlikely to use it or to follow the use and/or storage directions.

It may be difficult to obtain compositions that address some or all of these factors. It may be even more difficult to obtain anhydrous compositions that address some or all of these factors. As such, new compositions and methods for making such compositions may be desirable.

SUMMARY OF THE INVENTION

Provided according to some embodiments of the invention are anhydrous topical compositions that include at least one viscosity increasing agent, at least one organic solvent and at least one humectant. In some embodiments, the at least one viscosity increasing agent is present in the composition at a concentration in a range of 0.5 to 30 weight percent; the at least one organic solvent is present in the composition at a concentration in a range of 50 to 90 weight percent; and the at least one humectant is present in the composition at a concentration in a range of 2 to 20 weight percent.

In some embodiments of the invention, the topical anhydrous compositions further include at least one water repellant. In some embodiments, the at least one viscosity increasing agent is present in the composition at a concentration in a range of 0.5 to 30 weight percent; the at least one organic solvent is present in the composition at a concentration in a range of 50 to 90 weight percent; the at least one humectant is present in the composition at a concentration in a range of 2 to 20 weight percent; and the at least one water repellent is present in the composition at a concentration in a range of 0.5 to 15 weight percent.

In some embodiments, the topical anhydrous compositions further include a water reactive active pharmaceutical ingredient (API). In some embodiments, the water reactive API releases nitric oxide (NO) upon contact with water. In some embodiments, the water reactive API includes a diazeniumdiolate functional group. In some embodiments, the water reactive API includes a NO-releasing co-condensed silica.

Provided also in some embodiments are packaged nitric oxide-releasing topical gels having a shelf life of at least four weeks. Further provided are packaged nitric oxide-releasing topical gels having useful life of at least 30 days and in some embodiments at least 60 days.

A further aspect of the present invention comprises a method of treating a dermatological condition comprising applying an anhydrous topical composition of the present invention to the skin of a patient to treat the dermatological condition. In some embodiments, an anhydrous topical composition comprises at least one API. In other embodiments, an anhydrous topical composition comprises a vehicle and thus does not include at least one API. In certain embodiments, an anhydrous topical composition of the present invention is applied to the skin of a patient to treat acne.

BRIEF DESCRIPTION OF THE DRAWINGS

The following drawings are provided to illustrate various aspects of the present inventive concept and are not intended to limit the scope of the present invention unless specified herein.

DETAILED DESCRIPTION OF EMBODIMENTS OF THE INVENTION

Figure 1:
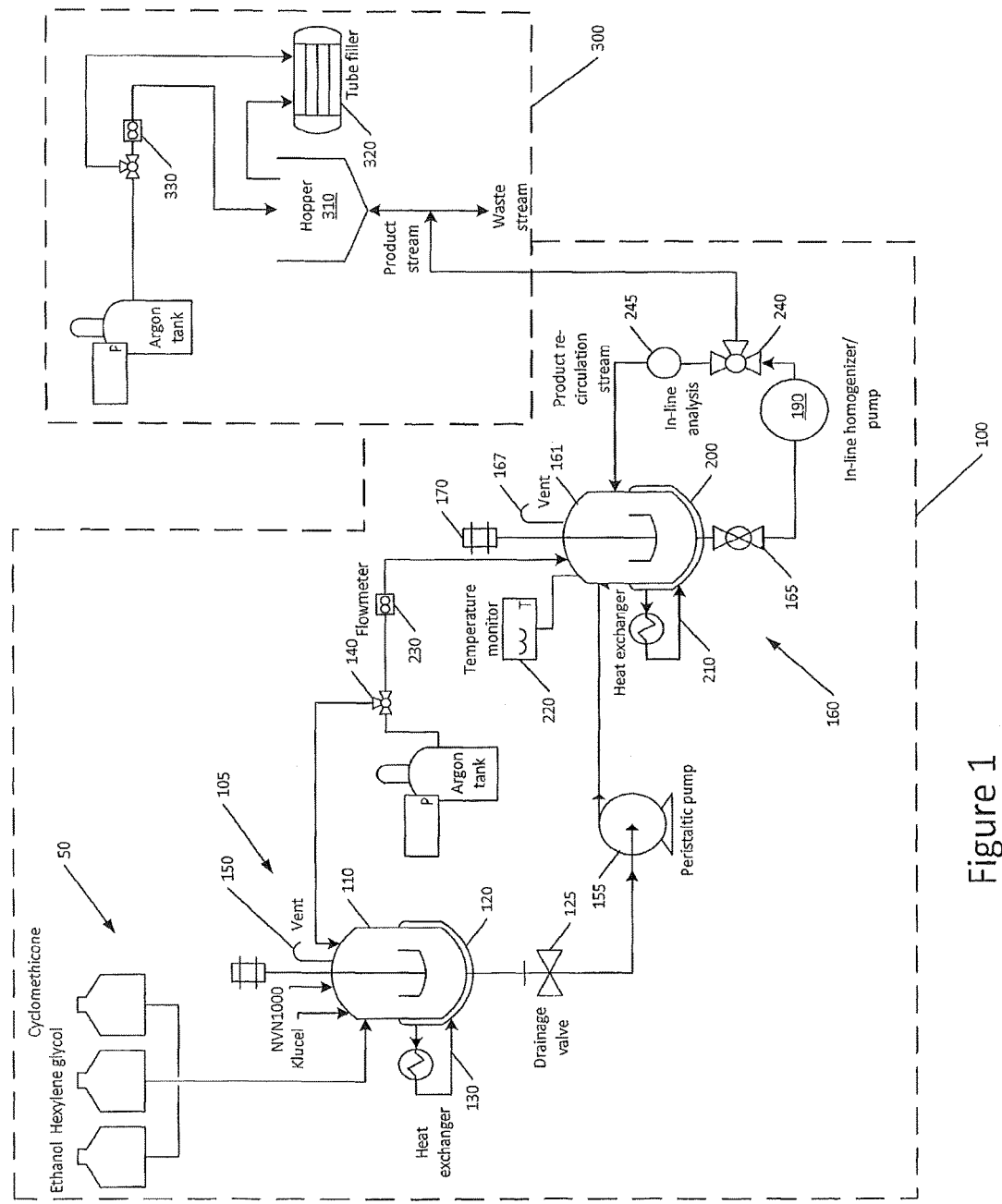
FIG. 1 is a process flow diagram illustrating manufacture and packaging of a topical therapeutic according to some embodiments of the present inventive concept.

The foregoing and other aspects of the present invention will now be described in more detail with respect to the description and methodologies provided herein. It should be appreciated that the invention may be embodied in different forms and should not be construed as limited to the embodiments set forth herein. Rather, these embodiments are provided so that this disclosure will be thorough and complete, and will fully convey the scope of the invention to those skilled in the art.

The terminology used in the description of the invention herein is for the purpose of describing particular embodiments only and is not intended to be limiting of the invention. As used in the description of the embodiments of the invention and the appended claims, the singular forms "a," "an" and "the" are intended to include the plural forms as well, unless the context clearly indicates otherwise. Also, as used herein, "and/or" refers to and encompasses any and all possible combinations of one or more of the associated listed items. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. When a range is employed (e.g., a range from x to y) it is it meant that the measurable value is a range from about x to about y, or any range therein, such as about $x_1$ to about $y_1$, etc. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Unless otherwise defined, all terms, including technical and scientific terms used in the description, have the same meaning as commonly understood by one of ordinary skill in the art to which this invention belongs.

All patents, patent applications and publications referred to herein are incorporated by reference in their entirety. In the event of conflicting terminology, the present specification is controlling.

The embodiments described in one aspect of the present invention are not limited to the aspect described. The embodiments may also be applied to a different aspect of the invention as long as the embodiments do not prevent these aspects of the invention from operating for its intended purpose.

Chemical Definitions

As used herein the term "alkyl" refers to C1-20 inclusive, linear (i.e., "straight-chain"), branched, or cyclic, saturated or at least partially and in some cases fully unsaturated (i.e., alkenyl and alkynyl) hydrocarbon chains, including for example, methyl, ethyl, propyl, isopropyl, butyl, isobutyl, tert-butyl, pentyl, hexyl, octyl, ethenyl, propenyl, butenyl, pentenyl, hexenyl, octenyl, butadienyl, propynyl, butynyl, pentynyl, hexynyl, heptynyl, and allenyl groups. "Branched" refers to an alkyl group in which a lower alkyl group, such as methyl, ethyl or propyl, is attached to a linear alkyl chain. Exemplary branched alkyl groups include, but are not limited to, isopropyl, isobutyl, tert-butyl. "Lower alkyl" refers to an alkyl group having 1 to 8 carbon atoms (i.e., a C1-8 alkyl), e.g., 1, 2, 3, 4, 5, 6, 7, or 8 carbon atoms. "Higher alkyl" refers to an alkyl group having 8 to 20 or more carbon atoms, e.g., 8, 9, 10, 11, 12, 13, 14, 15, 16, 17, 18, 19, 20, or more carbon atoms. In certain embodiments, "alkyl" refers, in particular, to C1-5 straight-chain alkyls. In other embodiments, "alkyl" refers, in particular, to C1-5 branched-chain alkyls.

Alkyl groups may optionally be substituted (a "substituted alkyl") with one or more alkyl group substituents, which may be the same or different. The term "alkyl group substituent" includes but is not limited to alkyl, substituted alkyl, halo, arylamino, acyl, hydroxyl, aryloxyl, alkoxyl, alkylthio, arylthio, aralkyloxyl, aralkylthio, carboxyl, alkoxycarbonyl, oxo, and cycloalkyl. There may be optionally inserted along the alkyl chain one or more oxygen, sulfur or substituted or unsubstituted nitrogen atoms, wherein the nitrogen substituent is hydrogen, lower alkyl (also referred to herein as "alkylaminoalkyl"), or aryl.

Thus, as used herein, the term "substituted alkyl" includes alkyl groups, as defined herein, in which one or more atoms or functional groups of the alkyl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto.

The term "aryl" is used herein to refer to an aromatic substituent that may be a single aromatic ring, or multiple aromatic rings that are fused together, linked covalently, or linked to a common group, such as, but not limited to, a methylene or ethylene moiety. The common linking group also may be a carbonyl, as in benzophenone, or oxygen, as in diphenylether, or nitrogen, as in diphenylamine. The term "aryl" specifically encompasses heterocyclic aromatic compounds. The aromatic ring(s) may comprise phenyl, naphthyl, biphenyl, diphenylether, diphenylamine and benzophenone, among others. In particular embodiments, the term "aryl" means a cyclic aromatic comprising 5 to 10 carbon atoms, e.g., 5, 6, 7, 8, 9, or 10 carbon atoms, and including 5- and 6-membered hydrocarbon and heterocyclic aromatic rings.

The aryl group may be optionally substituted (a "substituted aryl") with one or more aryl group substituents, which may be the same or different, wherein "aryl group substituent" includes alkyl, substituted alkyl, aryl, substituted aryl, aralkyl, hydroxyl, alkoxyl, aryloxyl, aralkyloxyl, carboxyl, acyl, halo, nitro, alkoxycarbonyl, aryloxycarbonyl, aralkoxycarbonyl, acyloxyl, acylamino, aroylamino, carbamoyl, alkylcarbamoyl, dialkylcarbamoyl, arylthio, alkylthio, alkylene, and —NR1R", wherein R1 and R" may each be independently hydrogen, alkyl, substituted alkyl, aryl, substituted aryl, and aralkyl.

Thus, as used herein, the term "substituted aryl" includes aryl groups, as defined herein, in which one or more atoms or functional groups of the aryl group are replaced with another atom or functional group, including for example, alkyl, substituted alkyl, halogen, aryl, substituted aryl, alkoxyl, hydroxyl, nitro, amino, alkylamino, dialkylamino, sulfate, and mercapto. Specific examples of aryl groups include, but are not limited to, cyclopentadienyl, phenyl, furan, thiophene, pyrrole, pyran, pyridine, imidazole, benzimidazole, isothiazole, isoxazole, pyrazole, pyrazine, triazine, pyrimidine, quinoline, isoquinoline, indole, carbazole, and the like.

"Cyclic" and "cycloalkyl" refer to a non-aromatic mono- or multicyclic ring system of 3 to 10 or more carbon atoms, e.g., 3, 4, 5, 6, 7, 8, 9, 10, or more carbon atoms. The cycloalkyl group may be optionally partially unsaturated. The cycloalkyl group also may be optionally substituted with an alkyl group substituent as defined herein, oxo, and/or alkylene. There may be optionally inserted along the cyclic alkyl chain one or more oxygen, sulfur or substituted or unsubstituted nitrogen atoms, wherein the nitrogen substituent is hydrogen, alkyl, substituted alkyl, aryl, or substituted aryl, thus providing a heterocyclic group. Representative monocyclic cycloalkyl rings include cyclopentyl, cyclohexyl, and cycloheptyl. Multicyclic cycloalkyl rings include adamantyl, octahydronaphthyl, decalin, camphor, camphane, and noradamantyl.

"Alkoxyl" refers to an alkyl-O— group wherein alkyl is as previously described. The term "alkoxyl" as used herein may refer to, for example, methoxyl, ethoxyl, propoxyl, isopropoxyl, butoxyl, t-butoxyl, and pentoxyl. The term "oxyalkyl" may be used interchangeably with "alkoxyl". In some embodiments, the alkoxyl has 1, 2, 3, 4, or 5 carbons.

"Aralkyl" refers to an aryl-alkyl group wherein aryl and alkyl are as previously described, and included substituted aryl and substituted alkyl. Exemplary aralkyl groups include benzyl, phenylethyl, and naphthylmethyl.

"Alkylene" refers to a straight or branched bivalent aliphatic hydrocarbon group having from 1 to 20 or more carbon atoms, e.g., 1, 2, 3, 4, 5, 6, 7, 8, 9, 10, 11, 12, 13, 14, 15, 16, 17, 18, 19, 20, or more carbon atoms. The alkylene group may be straight, branched or cyclic. The alkylene group also may be optionally unsaturated and/or substituted with one or more "alkyl group substituents." There may be optionally inserted along the alkylene group one or more oxygen, sulfur or substituted or unsubstituted nitrogen atoms (also referred to herein as "alkylaminoalkyl"), wherein the nitrogen substituent is alkyl as previously described. Exemplary alkylene groups include methylene (—CH2-); ethylene (—CH2-CH2-); propylene (—(CH2)3-); cyclohexylene (—C6H10-); —CH=CH—CH=CH—; —CH=CH—CH2-; wherein each of q and r is independently an integer from 0 to 20, e.g., 0, 1, 2, 3, 4, 5, 6, 7, 8, 9, 10, 11, 12, 13, 14, 15, 16, 17, 18, 19, or 20, or any range therein, and R is hydrogen or lower alkyl; methylenedioxyl (—O—CH2-

O—); and ethylenedioxyl (—O—(CH2)2-O—). An alkylene group may have 2 to 3 carbon atoms and may further have 6-20 carbons.

"Arylene" refers to a bivalent aryl group. An exemplary arylene is phenylene, which may have ring carbon atoms available for bonding in ortho, meta, or para positions with regard to each other, i.e., respectively. The arylene group may also be napthylene. The arylene group may be optionally substituted (a "substituted arylene") with one or more "aryl group substituents" as defined herein, which may be the same or different.

"Aralkylene" refers to a bivalent group that contains both alkyl and aryl groups. For example, aralkylene groups may have two alkyl groups and an aryl group (i.e., -alkyl-aryl-alkyl-), one alkyl group and one aryl group (i.e., -alkyl-aryl-) or two aryl groups and one alkyl group (i.e., -aryl-alkyl-aryl-).

The term "amino" and "amine" refer to nitrogen-containing groups such as NR3, NH3, NHR2, and NH2R, wherein R may be alkyl, branched alkyl, cycloalkyl, aryl, alkylene, arylene, aralkylene. Thus, "amino" as used herein may refer to a primary amine, a secondary amine, or a tertiary amine. In some embodiments, one R of an amino group may be a cation stabilized diazeniumdiolate (i.e., NONO—X+).

The terms "cationic amine" and "quaternary amine" refer to an amino group having an additional (i.e., a fourth) group, for example a hydrogen or an alkyl group bonded to the nitrogen. Thus, cationic and quarternary amines carry a positive charge.

The term "alkylamine" refers to the -alkyl-NH2 group.

The term "carbonyl" refers to the —(C=O)— group.

The term "carboxyl" refers to the —COOH group and the term "carboxylate" refers to an anion formed from a carboxyl group, i.e., —COO—.

The terms "halo", "halide", or "halogen" as used herein refer to fluoro, chloro, bromo, and iodo groups.

The term "hydroxyl" and "hydroxy" refer to the —OH group.

The term "hydroxyalkyl" refers to an alkyl group substituted with an —OH group.

The term "mercapto" or "thio" refers to the —SH group. The term "silyl" refers to groups comprising silicon atoms (Si).

As used herein the term "alkoxysilane" refers to a compound comprising one, two, three, or four alkoxy groups bonded to a silicon atom. For example, tetraalkoxysilane refers to Si(OR)4, wherein R is alkyl. Each alkyl group may be the same or different. An "alkylsilane" refers to an alkoxysilane wherein one or more of the alkoxy groups has been replaced with an alkyl group. Thus, an alkylsilane comprises at least one alkyl-Si bond. The term "fluorinated silane" refers to an alkylsilane wherein one of the alkyl groups is substituted with one or more fluorine atoms. The term "cationic or anionic silane" refers to an alkylsilane wherein one of the alkyl groups is further substituted with an alkyl substituent that has a positive (i.e., cationic) or a negative (i.e. anionic) charge, or may become charged (i.e., is ionizable) in a particular environment (i.e., in vivo).

The term "silanol" refers to a Si—OH group.

Pharmaceutical Compositions

One aspect of the present invention is directed to pharmaceutical compositions. Provided according to some embodiments of the invention are pharmaceutical compositions that include at least one active pharmaceutical ingredient (API). According to other embodiments of the present invention, provided are pharmaceutical compositions that do not include at least one API. Compositions described herein that do not have an API are referred to herein as "vehicles." Pharmaceutical compositions according to embodiments of the invention may, therefore, include at least one API or may be vehicles that do not include at least one API. In some embodiments, the pharmaceutical compositions are anhydrous, and in some embodiments, the pharmaceutical compositions are topical compositions. "Anhydrous," as used herein means that there is no direct addition of water to a composition of the present invention. However, those skilled in the art will recognize that water may be physically and/or chemically absorbed by a composition and/or by one or more ingredients in a composition at any time during the preparation, storage, and/or use of a composition of the present invention (i.e., indirect addition of water to the composition). In some embodiments, the term "anhydrous" means that a composition has a water content of less than 5% by weight of the composition or any range therein. A composition of the present invention may have a water content of less than 5, 4.5, 4, 3.5, 3, 2.5, 2, 1.5, 1, 0.5%, or any range therein, by weight of the composition. Water content may be measured by methods known to those of skill in the art, such as, but not limited to, Karl Fischer titration.

In some embodiments of the invention, the pharmaceutical composition is a topical composition, which may also be referred to as a "dermatological composition" herein. A topical composition may be applied to body surfaces, including skin, mucous membranes, scalp, hair and/or nails.

Provided according to embodiments of the invention are anhydrous pharmaceutical compositions that include excipients that include at least one viscosity agent, at least one solvent and at least one humectant. The term excipient refers to "inert" constituents of pharmaceutically acceptable compositions. The term "inert" indicates that such constituents are not considered active pharmaceutical ingredients, such as a nitric oxide-releasing compound or other antimicrobial compounds, anti-inflammatory agents, pain-relievers, immunosuppressants and vasodilators. However, as one of ordinary skill in the art will understand, the excipients may provide beneficial or therapeutic action to the skin (e.g., moisturize, provide anti-inflammatory effects) that may directly affect a topical ailment. The excipients may also indirectly affect the treatment of topical ailments by affecting the stability of NO-releasing compounds or other active pharmaceutical ingredients (APIs) within the compositions. It will be understood that any suitable combination of excipients may be present in the pharmaceutical compositions described herein.

Excipients for use in topical formulations are well-known in the art and examples may be found in the Handbook of Pharmaceutical Excipients (Rowe, R. C. et al., APhA Publications; 5th ed., 2005). Classes of excipients may include waxes, emollients, thickening agents/viscosity increasing agents, humectants, pH modifiers, water repelling agents, anti-foaming agents, surfactants, solubilizers, wetting agents, penetration enhancers, antioxidants, and solvents. The excipients may also be present in the topical composition at any suitable concentration. In some embodiments, the topical composition includes excipients at a concentration in a range from 70 to 99.99 weight percent.

Any suitable viscosity increasing agent may be used, and combinations of viscosity increasing agents may also be used. In some embodiments of the invention, the polymeric portion of the viscosity increasing agent may act as a visco-elastic substance and may retain the gel at the site of application, along with the APIs dispersed therein. Examples of viscosity increasing agents include co-polymers of carboxymethylcellulose and acrylic acid, N-vinylpyrrolidone, polyalkylene glycols (e.g., poly(ethylene glycol)), polyalkylene oxides (e.g., polyethylene oxide), polyvinyl alcohols, polyvinylpyrrolidone, polysiloxanes, poly(vinyl acetates), cellulose, derivatized celluloses, alginates, copolymers thereof and blends thereof. A specific example of a viscosity agent is hydroxypropylcellulose, such as Klucel® hydroxypropylcellulose (e.g., Klucel® MF Pharm grade).

Any suitable solvent or combinations of solvents may be used in the topical compositions. Examples of solvents include acetone, methyl alcohol, ethanol, isopropanol, butyl alcohol, ethyl acetate, dimethyl isosorbide, propylene glycol, glycerol, ethylene glycol, polyethylene glycol, diethylene glycol monoethyl ether or mixtures thereof. In particular examples, the solvent includes ethanol. In some embodiments, the solvent includes isopropyl alcohol. The skilled artisan will appreciate that the solvents may also be considered excipients, particularly at lower concentrations.

Any suitable humectant or combination of humectants may be used. Examples include glycols, such as diethylene glycol monoethyl ether; glycerols; sugar polyols, such as sorbitol, xylitol and maltitol; polyols such as polydextroses; quillaia, urea, and blends thereof. In particular examples, the humectant includes an alkylene glycol, such as hexylene glycol.

In some embodiments, the anhydrous topical compositions include at least one water repelling agent, also referred to as a water repellant. Examples of water repelling agents include silicones, such as cyclomethicone, dimethicone, simethicone, C26-28 alkyl dimethicone, C26-28 alkyl methicone, polyphenylsisquioxane, trimethylsiloxysilicate and crosspolymers of cyclopentasiloxane and dimethicone/vinyltrimethylsiloxysilicate, and blends thereof. The water repelling agent may be particularly useful in embodiments where the topical vehicle is used with a water-reactive API, such as a nitric oxide-releasing API whereby the nitric oxide is released in the presence of water (e.g., a diazeniumdialate). In other cases, such as when the API is not water sensitive, a water repelling agent may not be included.

In some embodiments of the invention, the anhydrous topical compositions may have a viscosity increasing agent concentration in a range from 0.5 to 30% by weight, a solvent concentration in a range from 50 to 90% by weight, and a humectant concentration in a range from 2 to 20% by weight. In some embodiments, the anhydrous topical compositions may also include a water repelling agent at a concentration in a range from 0.5% to 15% by weight. In some embodiments, the topical anhydrous compositions further include at least one API, for example, at a concentration in a range from 0.01 to 30% by weight, or any range therein.

In particular embodiments, the solvent is ethyl alcohol, 200 proof, anhydrous, the humectant is hexylene glycol available from Nexio Solutions; the water repelling agent is ST-cyclomethicone-5 NF available from Dow Corning Corp.; and the viscosity increasing agent is a hydroxypropylcellulose (HPC), such as Klucel® MF Pharm available from Ashland Aqualon.

In specific embodiments, the vehicle has the formulation of about 83.5% ethyl alcohol as a solvent, about 10% hexylene glycol as a humectant, about 2.5% ST-cyclomethicon-5 as a water repelling agent, about 2% HPC as a viscosity increasing agent, leaving about 2% available for inclusion of an API. In other embodiments the API is a nitric oxide donor. In other embodiments, the API is Nitricil™, a NO-releasing co-condensed silica, from Novan, Inc. In some embodiments, the total nitric oxide loading in the topical gel may be in a range from 0.01 to 5.0 wt/wt %. In some embodiments, the total nitric oxide loading in the topical gel is in a range from 0.24 to 0.36 wt/wt %.

In particular embodiments, the solvent is isopropyl alcohol, USP, the humectant is hexylene glycol available from Nexio Solutions; the water repelling agent is ST-cyclomethicone-5 NF available from Dow Corning Corp.; and the viscosity increasing agent is a hydroxypropylcellulose (HPC), such as Klucel® MF Pharm available from Ashland Aqualon.

In particular embodiments, the vehicle has the formulation of 86.5% less the percentage of API of isopropyl alcohol as a solvent, 10% hexylene glycol as a humectant, 2.5% ST-cyclomethicon-5 as a water repelling agent, and 1% HPC as a viscosity increasing agent. Decreasing the quantity of viscosity increasing agent in the formulation may allow for higher loadings of API while maintaining acceptable organoleptic properties, such as not feeling gritty. The quantity of API may be anywhere from 0.01% to 50% or any range therein, such as, but not limited to, from 0.1% to 30% or from 2% to 20%. In certain embodiments the API is a nitric oxide donor. In other embodiments, the API is Nitricil™, a NO-releasing co-condensed silica, from Novan, Inc. In some embodiments, the total nitric oxide loading in the topical gel may be in a range from 0.01 to 30 wt/wt % or any range therein, such as, but not limited to, 0.1 to 15 wt/wt %. In some embodiments, the total nitric oxide loading in the topical gel is in a range from 0.1 to 5 wt/wt % or any range therein. The total nitric oxide loading in a topical gel may be measured by methods known to those of skill in the art, including, but not limited to, using a nitric oxide analyzer, such as a Sievers 280i Nitric Oxide Analyzer.

For applications where the API is water reactive, such as a nitric oxide-releasing particle that releases nitric oxide in the presence of water, the inclusion of the water repelling agent may increase the API storage stability of the topical gel. In some embodiments, uniformly dispersing a water repellant with the API in a ratio of API to water repellant of from 0.01:1 to 30:1 and, in particular embodiments, 2 to 1, 4 to 1, 6 to 1, 8 to 1, 12 to 1 or 20 to 1, may, similarly, allow close association of the water repellant with the API and, thereby, improve stability of the topical gel.

For applications where the topical composition must absorb water, dissociate when in contact with an aqueous environment (e.g. on the surface of the skin), or utilize water as a mechanism for initiating drug release/delivery, the inclusion of a humectant may be used. For example, where the API is a diazeniumdiolated co-condensed silica particle, the humectant may be provided in a ratio of humectant to API of from 1:3 to 20:1 by weight to the API and, in some embodiments at a ratio from 5 to 1, 5 to 3, 1 to 1, 1 to 1.2 or 1 to 2 to the API. Uniformly dispersing the humectant with the API may allow for the close proximity of the humectant with the API in the final topical gel and, thereby, provide hydrophilic channels or access to moisture uptake in an anhydrous topical gel.

In compositions with water sensitive APIs (i.e., diazeniumdiolate), cellulose polymers may be useful as viscosity increasing agents because the crosslinking of the gel presents both a physical barrier to moisture diffusion and a hydrogen bonding network of water to protect it from getting to the water reactive functional groups. However, the cellulose polymer may not inhibit the release of nitric oxide in a moisture rich environment, such as on the skin of a patient. The degree of stability enhancement may be based on the weight percent of the cellulose polymer. Additional factors affecting nitric oxide stability may include the molecular weight of the cellulose. In some embodiments, the topical compositions may be considered pharmaceutically acceptable. A pharmaceutically acceptable composition, as defined herein, refers to a composition that is suitable for application to a subject, such as a human, without undue side effects such as toxicity or irritation to the skin. Undue side effects are those that render the composition unsuitable for application to a subject because the harm from the side effects outweighs the benefits of the composition.

In embodiments wherein the API includes a NO-releasing compound, the NO-releasing compounds may be present in pharmaceutically acceptable compositions according to embodiments of the invention at any suitable concentration, but in some embodiments, the NO-releasing compounds are present in the compositions at a concentration sufficient to elicit an improvement in, eliminate or prevent acne. In some embodiments, the concentration of NO-releasing compounds ranges from 0.1% to 30% w/w in the composition. In particular embodiments, the concentration of the NO-releasing compounds is less than 20% w/w in the composition or any range therein. In still further embodiments, the concentration of the NO-releasing compounds is less than 10% w/w in the composition or any range therein. In particular embodiments, the concentration of the NO-releasing compounds is 1%, 2%, 4%, or 8% w/w in the composition.

While pharmaceutically acceptable compositions that may be used in certain embodiments of the present inventive concept, in particular embodiments, a topical gel is provided. Topical gels according to the present inventive concept may be non-irritating to the skin, may provide noticeable results in a relatively short period of time, may be cosmetically elegant and/or may not bleach or otherwise stain clothing and other items that contact the product.

Additionally, to avoid a gritty feeling of the topical gel, the maximum particle size for a the API may be less than 100 μm, or any range therein, and, in some embodiments, less than 20 μm, and in further embodiments, less than 10 μm.

The topical vehicle and API may be readily spread by a patient and, therefore, may have a viscosity of from 250 cP to 50000 cP or any range therein, such as, but not limited to, 500 cP to 10000 cP or 1000 cP to 8000 cP. In some embodiments, the viscosity of the topical gel is about 7000 cP. The viscosity of the gel may be controlled by the amount of the viscosity increasing agent added to the gel. Too much of the agent and the gel will become too thick and difficult to spread.

The topical gel may also evaporate relatively quickly to avoid a feeling of greasiness and, in some cases, to provide a cooling sensation. Thus, the topical gel may have a relatively high level of volatiles. In some embodiments, the percent of volatiles by weight is greater than 55% or any range therein. In particular embodiments, the percent of volatiles by weight is about 55%, 66%, 74%, 80%, or 86%.

Additionally, the topical gel may have a "leave-on" layer or secondary formulation after evaporation of the volatiles that is spread substantially uniformly when the topical gel is spread on the skin. The percent non-volatiles may be from 2 to 45% by weight to provide a suitable leave-on layer. In some embodiments, the percent non-volatiles is about 14%, 17%, 23%, 31% or 41% by weight. In some embodiments, the leave-on layer comprises nitric oxide-releasing particles, hydroxypropylcellulose, and hexylene glycol.

A topical gel of the present invention may have a pH from 5 to 12, or any range therein, such as, but not limited to, from 7 to 12, 8 to 11, or 10 to 11. In certain embodiments, a topical gel may have a pH of about 5, 6, 7, 8, 9, 10, 11, or 12. In some embodiments, such as, but not limited to, embodiments comprising a water reactive API, the pH of a topical gel may change upon use (e.g., contact with the skin of a subject) and/or upon contact with water.

As described herein, selection of the ingredients may affect the stability and, therefore, the release of the nitric oxide from the API. Accordingly, the selected ingredients and their proportions may be selected to provide a desired stability and release profile for a given nitric oxide-releasing particle. Furthermore, as described below, the processing of the API and vehicle may also impact stability and release kinetics. For diazeniumdiolate NO-releasing APIs, considerations in determining the impact of the vehicle constituents and the processing include rate of release of nitric oxide desired, including the release profile desired, the type of ailment that the composition aims to treat, other APIs included in the composition and the stability desired.

Active Pharmaceutical Ingredients

Any suitable active pharmaceutical ingredient (API) or combinations of APIs may be included in the compositions according to embodiments of the invention. Examples of APIs include antimicrobial agents, anti-acne agents, anti-inflammatory agents, analgesic agents, anesthetic agents, antihistamine agents, antiseptic agents, immunosuppressants, antihemorrhagic agents, vasodilators, wound healing agents, anti-biofllm agents and mixtures thereof.

Examples of antimicrobial agents include penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenen, amikacin, netilmicin, fosfomycin, gentamycin, ceftriaxone, Ziracin, Linezolid, Synercid, Aztreonam, and Metronidazole, Epiroprim, Sanfetrinem sodium, Biapenem, Dynemicin, Cefluprenam, Cefoselis, Sanfetrinem celexetil, Cefpirome, Mersacidin, Rifalazil, Kosan, Lenapenem, Veneprim, Sulopenem, ritipenam acoxyl, Cyclothialidine, micacocidin A, carumonam, Cefozopran and Cefetamet pivoxil.

Examples of topical anti-acne agents include adapalene, azelaic acid, benzoyl peroxide, clindamycin and clindamycin phosphate, doxycycline, erythromycin, keratolytics such as salicylic acid and retinoic acid (Retin-A"), norgestimate, organic peroxides, retinoids such as isotretinoin and tretinoin, sulfacetamide sodium, and tazarotene. Particular anti-acne agents include adapalene, azelaic acid, benzoyl peroxide, clindamycin (e.g., clindamycin phosphate), doxycycline (e.g., doxycycline monohydrate), erythromycin, isotretinoin, norgestimate, sulfacetamide sodium, tazarotene, etretinate and acetretin.

Examples of antihistamine agents include diphenhydramine hydrochloride, diphenhydramine salicylate, diphenhydramine, chlorpheniramine hydrochloride, chlorpheniramine maleate isothipendyl hydrochloride, tripelennamine hydrochloride, promethazine hydrochloride, methdilazine hydrochloride, and the like. Examples of local anesthetic agents include dibucaine hydrochloride, dibucaine, lidocaine hydrochloride, lidocaine, benzocaine, p-buthylaminobenzoic acid 2-(die-ethylamino)ethyl ester hydrochloride, procaine hydrochloride, tetracaine, tetracaine hydrochloride, chloroprocaine hydrochloride, oxyprocaine hydrochloride, mepivacaine, cocaine hydrochloride, piperocaine hydrochloride, dyclonine and dyclonine hydrochloride.

Examples of antiseptic agents include alcohols, quaternary ammonium compounds, boric acid, chlorhexidine and chlorhexidine derivatives, iodine, phenols, terpenes, bactericides, disinfectants including thimerosal, phenol, thymol, benzalkonium chloride, benzethonium chloride, chlorhexidine, povidone iode, cetylpyridinium chloride, eugenol and trimethylammonium bromide.

Examples of anti-inflammatory agents include nonsteroidal anti-inflammatory agents (NSAIDs); propionic acid derivatives such as ibuprofen and naproxen; acetic acid derivatives such as indomethacin; enolic acid derivatives such as meloxicam, acetaminophen; methyl salicylate; monoglycol salicylate; aspirin; mefenamic acid; flufenamic acid; indomethacin; diclofenac; alclofenac; diclofenac sodium; ibuprofen; ketoprofen; naproxen; pranoprofen; fenoprofen; sulindac; fenclofenac; clidanac; flurbiprofen; fentiazac; bufexamac; piroxicam; phenylbutazone; oxyphenbutazone; clofezone; pentazocine; mepirizole; tiaramide hydrochloride; steroids such as clobetasol propionate, bethamethasone dipropionate, halbetasol proprionate, diflorasone diacetate, fluocinonide, halcinonide, amcinonide, desoximetasone, triamcinolone acetonide, mometasone furoate, fluticasone proprionate, betamethasone diproprionate, triamcinolone acetonide, fluticasone propionate, desonide, fluocinolone acetonide, hydrocortisone vlaerate, prednicarbate, triamcinolone acetonide, fluocinolone acetonide, hydrocortisone and others known in the art, predonisolone, dexamethasone, fluocinolone acetonide, hydrocortisone acetate, predonisolone acetate, methylpredonisolone, dexamethasone acetate, betamethasone, betamethasone valerate, flumetasone, fluorometholone, beclomethasone diproprionate, fluocinonide, topical corticosteroids, and may be one of the lower potency corticosteroids such as hydrocortisone, hydrocortisone-21-monoesters (e.g., hydrocortisone-21-acetate, hydrocortisone-21-butyrate, hydrocortisone-21-propionate, hydrocortisone-21-valerate, etc.), hydrocortisone-17,21-diesters (e.g., hydrocortisone-17,21-diacetate, hydrocortisone-17-acetate-21-butyrate, hydrocortisone-17,21-dibutyrate, etc.), alclometasone, dexamethasone, flumethasone, prednisolone, or methylprednisolone, or may be a higher potency corticosteroid such as clobetasol propionate, betamethasone benzoate, betamethasone dipropionate, diflorasone diacetate, fluocinonide, mometasone furoate, triamcinolone acetonide.

Examples of analgesic agents include alfentanil, benzocaine, buprenorphine, butorphanol, butamben, capsaicin, clonidine, codeine, dibucaine, enkephalin, fentanyl, hydrocodone, hydromorphone, indomethacin, lidocaine, levorphanol, meperidine, methadone, morphine, nicomorphine, opium, oxybuprocaine, oxycodone, oxymorphone, pentazocine, pramoxine, proparacaine, propoxyphene, proxymetacaine, sufentanil, tetracaine and tramadol.

Examples of anesthetic agents include alcohols such as phenol; benzyl benzoate; calamine; chloroxylenol; dyclonine; ketamine; menthol; pramoxine; resorcinol; troclosan; procaine drugs such as benzocaine, bupivacaine, chloroprocaine; cinchocaine; cocaine; dexivacaine; diamocaine; dibucaine; etidocaine; hexylcaine; levobupivacaine; lidocaine; mepivacaine; oxethazaine; prilocaine; procaine; proparacaine; propoxycaine; pyrrocaine; risocaine; rodocaine; ropivacaine; tetracaine; and derivatives, such as pharmaceutically acceptable salts and esters including bupivacaine HCl, chloroprocaine HCl, diamocaine cyclamate, dibucaine HCl, dyclonine HCl, etidocaine HCl, levobupivacaine HCl, lidocaine HCl, mepivacaine HCl, pramoxine HCl, prilocaine HCl, procaine HCl, proparacaine HCl, propoxycaine HCl, ropivacaine HCl, and tetracaine HCl.

Examples of antihemorrhagic agents include thrombin, phytonadione, protamine sulfate, aminocaproic acid, tranexamic acid, carbazochrome, carbaxochrome sodium sulfanate, rutin and hesperidin.

In some embodiments of the invention, the active pharmaceutical ingredient (API) includes a compound that releases nitric oxide (NO). Any suitable NO-releasing compound may be used. In some embodiments, the NO-releasing compound includes a small molecule compound that includes an NO donor group. Small molecule compounds are defined herein as compounds having a molecular weight of less than 500 daltons, and include organic and/or inorganic small molecules. In some embodiments, the NO-releasing compound includes a macromolecule that includes an NO donor group. A macromolecule is defined herein as any compound that has a molecular weight of 500 daltons or greater. Any suitable macromolecule may be used, including crosslinked or non-crosslinked polymers, dendrimers, metallic compounds, organometallic compounds, inorganic-based compounds, and other macromolecular scaffolds. In some embodiments, the macromolecule has a nominal diameter ranging from 0.1 nm-100 μm and may comprise the aggregation of two or more macromolecules, whereby the macromolecular structure is further modified with a NO donor group.

In some embodiments of the invention, the NO donor of the NO-releasing compound releases nitric oxide upon exposure to an external condition, such as light, heat, water, acid, base, and the like. For example, in some embodiments, the NO-releasing compound includes a diazeniumdiolate functional group as an NO donor. The diazeniumdiolate functional group may produce nitric oxide under certain conditions, such as upon exposure to water. As another example, in some embodiments, the NO-releasing compound includes a nitrosothiol functional group as the NO donor. The NO donor may produce nitric oxide under certain conditions, such as upon exposure to light. Examples of other NO donor groups include nitrosamine, hydroxyl nitrosamine, hydroxyl amine and hydroxyurea. Any suitable combination of NO donors and/or NO-releasing compounds may also be used in the methods described herein. Additionally, the NO donor may be incorporated into or onto the small molecule or macromolecule through covalent and/or non-covalent interactions.

In some embodiments of the invention, the NO-releasing compounds may be in the form of NO-releasing particles, such as those described in U.S. Publication No. 2009/0214618, the disclosure of which is incorporated by reference herein in its entirety. Such particles may be prepared by methods described therein.

The NO-releasing compound may release nitric oxide by any suitable mechanism, including via reaction with water and/or thermal degradation. Examples of NO-releasing functional groups that may be included in the NO-releasing compound include, but are not limited to, diazeniumdiolate, nitrosamine, hydroxyl nitrosamine, nitrosothiol, hydroxyl amine, hydroxyurea, and metal nitrosyl complexes. Other NO-releasing functional groups that are capable of releasing nitric oxide in a therapeutic manner, such as acidified nitrite, may also be utilized.

The NO-releasing compound may be a small molecule compound, an oligomer and/or a polymer and may be in any suitable physical form, such as, but not limited to, a particle, coating, film, liquid, solution and the like. In some embodiments, the nitric oxide-releasing compound comprises diazeniumdiolate-functionalized polysiloxane macromolecules as described above. Other non-limiting examples of NO-releasing compounds include NO-releasing zeolites as described in United States Patent Publication Nos. 2006/0269620 or 2010/0331968; NO-releasing metal organic frameworks (MOFs) as described in United States Patent Application Publication Nos. 2010/0239512 or 2011/0052650; NO-releasing multi-donor compounds as described in U.S. Provisional Patent Application Ser. No. 61/526,918 entitled "Tunable Nitric Oxide-Releasing Macromolecules Having Multiple Nitric Oxide Donor Structures"; NO-releasing dendrimers or metal structures as described in U.S. Publication No. 2009/0214618; nitric oxide releasing coatings as described in U.S. Publication No. 2011/0086234; and compounds as described in U.S. Publication No. 2010/0098733. The disclosures of each of the references in this paragraph are incorporated herein by reference in their entirety. Additionally, NO-releasing macromolecules may be fabricated as described in International Application No. PCT/US2012/022048 entitled "Temperature Controlled Sol-Gel Co-Condensation" filed Jan. 20, 2012, the disclosure of which is incorporated herein by reference in its entirety.

As an example, in some embodiments of the invention, the NO-releasing particles include NO-loaded precipitated silica. The NO-loaded precipitated silica may be formed from nitric oxide donor modified silane monomers into a co-condensed siloxane network. In one embodiment of the invention, the nitric oxide donor is an N-diazeniumdiolate.

In some embodiments, the nitric oxide donor may be formed from an aminoalkoxysilane by a pre-charging method, and the co-condensed siloxane network may be synthesized from the condensation of a silane mixture that includes an alkoxysilane and the aminoalkoxysilane to form a nitric oxide donor modified co-condensed siloxane network. As used herein, the "pre-charging method" means that aminoalkoxysilane is "pretreated" or "precharged" with nitric oxide prior to the co-condensation with alkoxysilane. In some embodiments, the precharging nitric oxide may be accomplished by chemical methods. In another embodiment, the "pre-charging" method may be used to create co-condensed siloxane networks and materials more densely functionalized with NO-donors.

The co-condensed siloxane network may be silica particles with a uniform size, a collection of silica particles with a variety of size, amorphous silica, a fumed silica, a nanocrystalline silica, ceramic silica, colloidal silica, a silica coating, a silica film, organically modified silica, mesoporous silica, silica gel, bioactive glass, or any suitable form or state of silica.

In some embodiments, the alkoxysilane is a tetraalkoxysilane having the formula Si(OR)4, wherein R is an alkyl group. The R groups may be the same or different. In some embodiments the tetraalkoxysilane is selected as tetramethyl orthosilicate (TMOS) or tetraethyl orthosilicate (TEOS). In some embodiments, the aminoalkoxysilane has the formula: R"—(NH—R')n-Si(OR)3, wherein R is alkyl, R' is alkylene, branched alkylene, or aralkylene, n is 1 or 2, and R" is selected from the group consisting of alkyl, cycloalkyl, aryl, and alkylamine.

In some embodiments, the aminoalkoxysilane may be selected from N-(6-aminohexyl)aminopropyltrimethoxysilane (AHAP3); N-(2-aminoethyl)-3-aminopropyltrimethoxysilane (AEAP3); (3-trimethoxysilylpropyl)di-ethylenetriamine (DET3); (aminoethylaminomethyl)phenethyltrimethoxysilane (AEMP3); [3-(methylamino)propyl]trimethoxysilane (MAP3); N-butylaminopropyltrimethoxysilane(n-BAP3); t-butylaminopropyltrimethoxysilane(t-BAP3); N-ethylaminoisobutyltrimethoxysilane (EAiB3); N-phenylamino-propyltrimethoxysilane (PAP3); and N-cyclohexylaminopropyltrimethoxysilane (cHAP3).

In some embodiments, the aminoalkoxysilane has the formula: NH[R'—Si(OR)3]2, wherein R is alkyl and R' is alkylene. In some embodiments, the aminoalkoxysilane may be selected from bis(3-triethoxysilylpropyl)amine, bis-[3-(trimethoxysilyl)propyl]amine and bis-[(3-trimethoxysilyl)propyl]ethylenediamine.

In some embodiments, as described herein above, the aminoalkoxysilane is precharged for NO-release and the amino group is substituted by a diazeniumdiolate. Therefore, in some embodiments, the aminoalkoxysilane has the formula: R"—N(NONO—X+)—R'—Si(OR)3, wherein R is alkyl, R' is alkylene or aralkylene, R" is alkyl or alkylamine, and X+ is a cation selected from the group consisting of Na+, K+ and Li+.

The composition of the siloxane network, (e.g., amount or the chemical composition of the aminoalkoxysilane) and the nitric oxide charging conditions (e.g., the solvent and base) may be varied to optimize the amount and duration of nitric oxide release. Thus, in some embodiments, the composition of the silica particles may be modified to regulate the half-life of NO release from silica particles.

In another embodiment, the amino group of aminoalkoxysilane is substituted with a diazeniumdiolate, and the aminoalkoxysilane having a formula of R"—N(NONO—X+)—R'—Si(OR)3, wherein: R is alkyl, R' is alkylene or aralkylene, R" is alkyl or alkylamine, and X+ is a cation selected from the group consisting of Na+ and K+.

In some embodiments of the invention, the particle size of the NO-releasing particles is in a range from 20 nm to 10 μm. The particle size may be tailored to minimize or prevent toxicity and penetration through the epidermis (or compromised dermis) and into the blood vessels. In particular embodiments, the particle size is distributed around a mean particle size of less than 10 μm, or any range therein, to allow the particle to enter a follicle. In further embodiments, the particle size is distributed around a mean particle size of less than 8 μm, or any range therein. In other embodiments, the particle size is distributed around a mean particle size of greater than 10 μm, or any range therein, to prevent the particle from entering the follicle.

In still further embodiments, a mixture of particles with mean particle sizes distributed around two or more mean particle sizes may be provided. For example, a mixture of particles having a particle size distributed around a mean particle size of less than 10 μm to allow the particle to enter a follicle may be mixed with particles having a particle size distributed around a mean particle size of greater than 10 μm to prevent the particle from entering the follicle. The particles may have the same nitric oxide release profiles or different nitric oxide release profiles. For example, the smaller particles may have a release profile tailored to enhance their ability to moderate sebum production and/or abnormal keratinization and the larger particles may have a release profile tailored to enhance their ability to kill bacteria, promote wound healing, reduce scarring or other desirable therapeutic effect provided by nitric oxide. Other combinations and multiple combinations could also be provided.

Synthetic Methods and Apparatus

The compositions described herein may be made by any suitable method. However, in some embodiments, the compositions may be manufactured by a method described herein and in U.S. Provisional Patent Application Ser. Nos. 61/504,626 and 61/610,179, both entitled "Methods of Manufacturing Topical Compositions and Apparatus For Same," filed Jul. 5, 2011 and Mar. 13, 2012, respectively, which are hereby incorporated by reference herein in their entirety.

In some embodiments, such methods include homogenizing a first excipient composition that includes a viscosity increasing agent and at least one solvent to form a first premix composition; separately homogenizing at least one active pharmaceutical ingredient (API) and a second excipient composition to form a second premix composition; and combining the first premix composition and the second premix composition to form the anhydrous topical composition. The pre-mixing of constituents may increase the stability of the API and provide uniformity of the dispersion of the constituents throughout the final topical composition. In some embodiments, the first excipient composition includes at least one viscosity agent, at least one solvent and at least one humectant, while the second excipient composition includes at least one water repellant and at least one humectant. In some cases, the humectant may be divided between the first excipient composition and the second excipient composition so that the humectant may aid in swelling of the viscosity increasing agent.

Any suitable homogenization mechanism may be used. Examples of homogenization devices include mechanical overhead agitation such as propeller, anchor, pitch blade, rotor-stator, rotating blades, ultrasonic devices, in-line and high pressure homogenizers. Any of these methods may be used, and multiple methods may be used in combination in some embodiments. Homogenization of the premix compositions may provide a final topical composition that has desirable API stability and blend homogeneity. In some embodiments of the present invention, an in-line homogenizer may be used. Homogenization may be carried out continuously throughout out the mixing of a composition and/or portion of a composition (e.g., a first and/or second excipient composition). In some embodiments, homogenization may be carried out intermittently throughout out the mixing of a composition and/or portion of a composition (e.g., a first and/or second excipient composition). In certain embodiments, homogenization may be carried out intermittently in durations of 15, 14, 13, 12, 11, 10, 9, 8, 7, 6, 5, 4, 3, 2, or 1 minutes, or any range therein, every 15, 14, 13, 12, 11, 10, 9, 8, 7, 6, 5, 4, 3, 2, 1 minutes, or any range therein.

In particular embodiments of the present invention, a homogenization method and/or device may be used that maintains the active pharmaceutical ingredient (e.g., a water reactive active pharmaceutical ingredient) below a temperature at which the active pharmaceutical ingredient could degrade. An active pharmaceutical ingredient may degrade at a particular temperature if maintained at that temperature for a specific duration of time. Accordingly, in some embodiments of the present invention, the duration of time an active pharmaceutical ingredient is maintained at a particular temperature, is below the time period at which the active ingredient could degrade at that temperature. In certain embodiments of the present invention, for the entire homogenization process, the active pharmaceutical ingredient is kept at a temperature that does not exceed the temperature at which the active pharmaceutical ingredient could degrade.

In some embodiments, homogenization is performed at a temperature in a range from −15° C. to 30° C., or any range therein, such as, but not limited to, −5° C. to 25° C., 0° C. to 10° C., 10° C. to 20° C., or 15° C. to 25° C. In some embodiments, the homogenization is performed at room temperature. In other embodiments, the homogenization is performed below room temperature.

In some embodiments, homogenization is performed in a dry, inert atmosphere, such that water and oxygen are substantially absent from the homogenization vessel.

In some embodiments, homogenizing the first excipient composition that includes the at least one viscosity increasing agent and the at least one solvent includes adding the viscosity increasing agent to the solvent at a relatively rapid rate, such as at a rate in a range of 0.5 to 50 g of viscosity increasing agent per min per liter solvent. In one embodiment, the rate is 15 g of viscosity increasing agent per min per liter solvent. In some embodiments where a humectant is added to the first excipient composition, a portion of the humectant may be homogenized with the at least one solvent, and then the at least one viscosity increasing agent may be added to the mixture and the first excipient composition may be homogenized. In other embodiments, a portion of the humectant, at least one solvent, and at least one viscosity increasing agent are added and homogenized together at the same time. One or more portions of the humectant, such as 1, 2, 3, or more, may be added to the first excipient composition at different times. Accordingly, when a humectant is added to the first excipient composition, the humectant may be portioned into 2, 3, 4, or more equal and/or unequal portions, and one or more portions of the humectant may be added to the first excipient composition. For example, a humectant may be divided into three equal and/or unequal portions, and two of the three portions may be added to the first excipient composition at different times with the remaining portion added to the second excipient composition.

The rapid addition of a viscosity increasing agent such as hydroxypropyl cellulose to the solvent is contrary to the typical practice in the industry that would suggest slow addition of a viscosity increasing agent such as hydroxypropyl cellulose to the solvent to avoid clumping. In contrast, the present inventors have found that by using the homogenization apparatus described herein as a premixing vessel, the viscosity increasing agent may be rapidly added. In fact, in some cases, rapid addition may result in a more homogeneous mixture. In some embodiments, the homogenization of the first excipient composition and the at least one solvent may be performed at a rate of 2,500 to 10,000 RPM, for example, with an IKA T-50 UltraTurax rotor stator device or equivalent mixing conditions utilizing alternative homogenization devices.

In some embodiments, homogenizing the second excipient composition is performed at a rate of 2500 to 10,000 rpm. In a particular embodiment the rate is 7,500 RPM utilizing the rotor stator configuration described above. Homogenization may be achieved by using an apparatus described herein. In some embodiments of the invention, the homogenization apparatus includes a vessel and a rotor-stator therein. In some embodiments, the ratio of the height of the reactive portion of the vessel to the width of the vessel is in a range of 1:2 to 1:1. In some embodiments, the widest portion of the rotor-stator has a diameter that is 5 to 50% of the width of the vessel. The vessel may be temperature controlled and may include an inlet and outlet for an inert gas. The vessel may be made of any suitable material, including, for example, glass, stainless steel, polytetrafluoroethylene, and other non-reactive materials. Particular embodiments of the homogenization apparatus will be described in detail below.

Once the two premix compositions are prepared, they may be combined and mixed. In some embodiments, the premix compositions are mixed at a rate in a range of 10 to 50 RPM. In addition to mixing the two premix compositions, the combined composition may be homogenized, for example, under high shear using IKA Labor Pilot 2000/4 in-line homogenizer operating at a rate in a range of 2,000 to 24,000 RPM, allowing material to be recirculated at a rate of up to 4 gallons per minute, or equivalent conditions with alternative homogenization devices. Such a homogenization process may smooth, deagglomerate, reduce particle size, increase blend uniformity of excipient and active pharmaceutical ingredients, improve viscosity uniformity, reduce segregation of suspended particulates, and/or improve API stability.

Process parameters for an exemplary homogenization process are provided in Table 1.

TABLE 1

Exemplary process parameters

| Process Parameter | Setting/Range |
| --- | --- |
| Pre-mixing vessel temperature | 18° C. to 22° C. |
| Main vessel temperature | 18° C. to 22° C. |
| Inert gas flow rate | about 0.2 liters per minute |
| Rate of addition for hydroxypropyl cellulose | 1 minute or less |
| Mixer/agitator speed setting for the main vessel | 75 Hz to 90 Hz |
| Mixing time for the first excipient composition | 30 minutes or more |
| In-line homogenization time for the first excipient composition | homogenize in about 5 minute durations every 5 to 10 minutes throughout the mixing time for the first excipient composition |
| Rotor-stator homogenization time for the second excipient composition | 2 minutes or more |
| Mixing time for the composition | 30 minutes or more |
| In-line homogenization time for the composition | homogenize in about 2 minute durations every 5 to 10 minutes throughout the mixing time for the composition |

Exemplary Methods and Apparatus for Manufacturing Topical Compositions

FIG. 1 is a detailed drawing of a system 100 for the manufacture of formulations according to some embodiments of the present invention. As seen in FIG. 1, the system 100 includes a pre-mixing vessel 105 that is provided by a rotor-stator homogenizer 110 in a single jacketed vessel 120 that is connected to a circulator 130 for temperature control. The jacketed vessel 120 may be operated under an blanket of inert gas, such as argon, with a rotameter 230 used to control the rate of inert gas addition by controlling the flow from one of the two outputs of a three-way valve. A vent line 150 is also present to exhaust excess inert gas. Raw materials are introduced from holding vessels 50 to the pre-mixing vessel 105.

The pre-mixing vessel 105 is used for two primary purposes in the system 100: (1) to provide a forced wetting mechanism for excipients such as, but not limited to, viscosity increasing agents such as hydroxypropyl cellulose (HPC) in a suspension consisting of solvents and excipients to produce a gel, ointment or cream; and (2) to disperse an active pharmaceutical ingredient, such as those described herein, in a suspension of the active pharmaceutical ingredient and solvents or excipients. The pre-mixing vessel 105 has an oversize valve 125 to prevent blockages during transfer of suspensions to a mixing vessel (kettle) 160. For example, the mixing vessel 160 may be a 15 Liter top driven mixing vessel available from Lee Industries. The transfer of suspensions between the pre-mixing vessel 105 and the mixing vessel 160 is carried out by using a peristaltic pump 155 at a controlled rate. The peristaltic pump may, for example, be a Masterflex LS available from Cole-Parmer, or similar. The transfer rate of excipients into the system 100 for pre-mixing may also be important to compounding in the mixing vessel 160.

The mixing vessel 160 includes kettle 161, a motor 170 to drive an overhead anchor agitator with paddles 180 and has an in-line homogenizer 190 that is connected to the bottom ball valve 165 of the mixing vessel 160. The in-line homogenizer 190 may, for example, be a Labor Pilot 2000/4 available from IKA-Werk, or similar. The mixing vessel 160 includes a jacket 200 that is connected to a circulator 210 to maintain temperature control. The mixing vessel 160 also has a RTD sensor 166 to monitor temperature in the kettle 161 and is recorded automatically using a recorder 220, such as a Honeywell chart recorder. The contents of the kettle 161 may also be under an inert gas blanket with a rotometer 230 used to control the rate of inert gas addition. A vent line 167 is also present on the mixing vessel 160 to exhaust excess inert gas. The in-line homogenizer 190 is used for process intensification from an enhanced mixing perspective, particularly during semi-solids compounding. Semi-solids products may also be discharged via the use of the in-line homogenizer 190 through the use of a three-way valve 240.

Additionally, as illustrated in FIG. 1, optional in-line processing/analysis equipment 245 may be provided. For example, the in-line processing/analysis equipment 245 may include a viscometer to measure viscosity, a Ramen spectrometer, a pH meter, lighting devices to pre-age or otherwise process a composition, a colorimeter to measure the color and/or uniformity of the gel or other such in-line analysis equipment.

The system 100 may allow for excipients to be dispersed uniformly without agglomeration and lumping. A homogeneous solution, suspension, gel, ointment, emulsion, and cream, or other pharmaceutical composition, may be manufactured using this device. Furthermore, the system 100 using the homogenizer allows for active pharmaceutical ingredients to be dispersed in a suspension to improve blend uniformity and thus prevent agglomeration formation and potential segregation. The in-line homogenizer 190 may be used to further aid the formation of a semi-solid formulation that is homogenous and uniform in terms of excipient and active pharmaceutical ingredient distribution. In some embodiments, it may be desirable to use an inert gas environment in both the pre-mixing vessel 105 and mixing vessel 160 is to prevent moisture from entering. As such, such an apparatus may be useful for making moisture-sensitive, or otherwise anhydrous, formulations.

Figure 2:
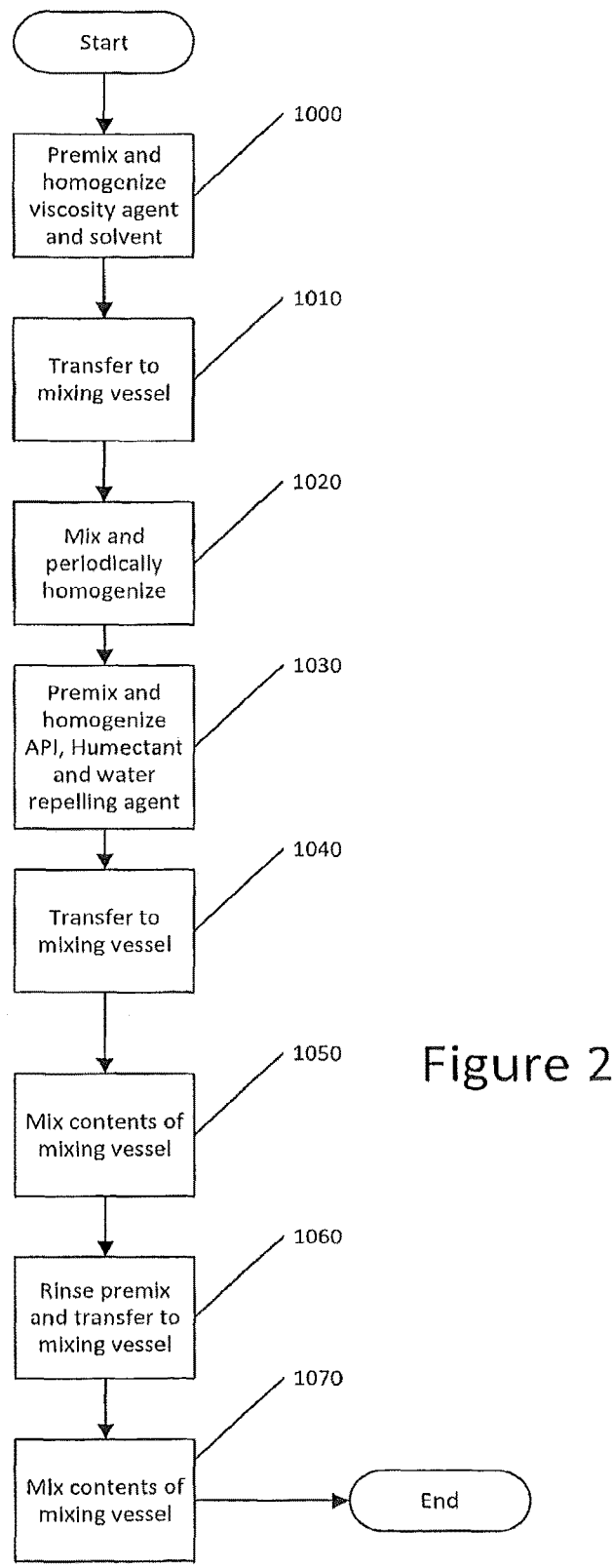
FIG. 2 is a flowchart illustrating operations/steps in a process for manufacturing a topical therapeutic according to some embodiments of the present inventive concept.

Operation of the system 100 will now be described with reference to an exemplary manufacturing process for producing a topical composition. FIG. 2 is a flowchart illustration of steps/operations that may be carried out according to some embodiments of the present invention. As seen in FIG. 2, the first excipient composition is premixed in the pre-mixing vessel 100 (block 1000) and transferred to the mixing vessel 160 (block 1010), for example, by the peristaltic pump 155. The forced wetting of the viscosity increasing agent with the homogenizer 110 of the pre-mixing vessel 105 may allow for the rapid combination of materials which, otherwise, would take substantially longer to mix. The contents of the mixing vessel 160 are mixed and periodically homogenized (block 1020), for example, by recirculating the contents of the mixing vessel 160 through the in-line homogenizer 190.

In block 1030, the API and the second excipient composition are premixed and homogenized in the homogenizer 110. Premixing these constituents may improve the uniformity of them in the final gel as well as closely associating the API with excipients such as the humectant and the water repelling agent which, in the case of a water reactive API, may improve the stability of the API in the final topical composition. The pre-mixed contents of the homogenizer 110 are then transferred to the mixing vessel 160 via the peristaltic pump 155 (block 1040) and the contents mixed in the mixing vessel 160 (block 1050). The premix homogenizer 110 is then rinsed with the solvent and the contents transferred to the mixing vessel 160 (block 1060). The contents of the mixing vessel are then mixed until the desired uniformity is obtained (block 1070).

Figure 3:
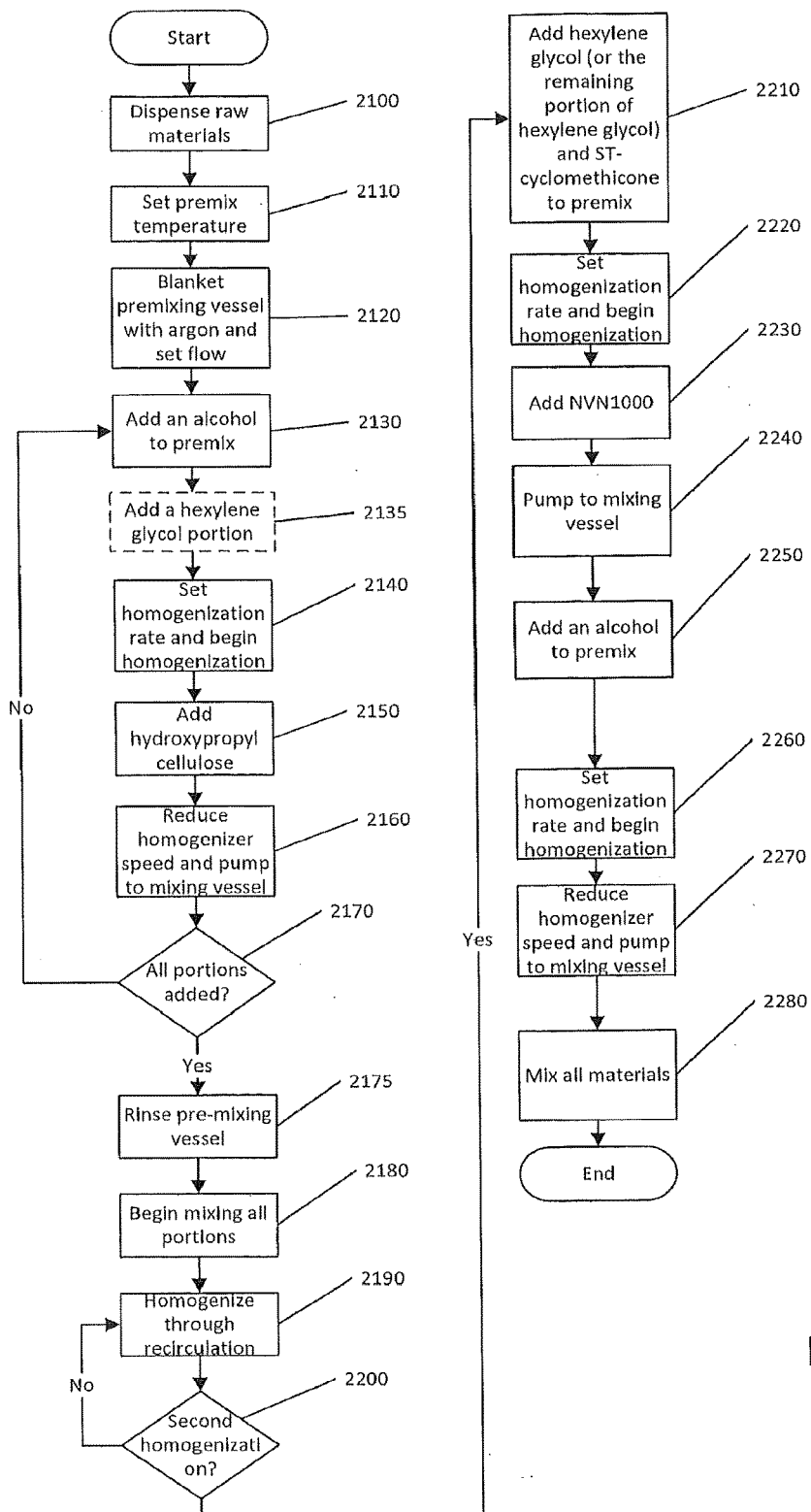
FIG. 3 is a flowchart illustrating further operations/steps in a process for manufacturing a topical therapeutic according to some embodiments of the present inventive concept

FIG. 3 is a more detailed flowchart of operations for a particular system 100 according to some embodiments of the present inventive concept. As seen in FIG. 3, operations begin by dispensing raw materials for use in the process (block 2100). In particular embodiments for the exemplary system of FIG. 1, the raw materials may be dispensed as multiple portions of the same raw material. Such portions may be based on the batch size and the dimensions of the particular equipment utilized. Thus, what is described herein with reference to multiple sub-processes could be combined into fewer sub-process or more sub-processes depending on the particular equipment utilized and batch size. In some embodiments, for the initial mixing operations, the dispensed raw materials are ethyl alcohol and/or isopropyl alcohol as the solvent and Klucel® hydroxypropyl cellulose as the viscosity increasing agent.

The temperature of the pre-mixing vessel 105 and the mixing vessel 160 are set to 20° C.+/−2° C. via the jacket 120 and the recirculation system 130 and the jacket 200 and recirculating system 210 (block 2110). The pre-mixing vessel 105 and mixing vessel 160 are blanketed with argon gas and the flow set through the valve 140 to provide about 0.2 liters of argon per minute (block 2120). The alcohol is added to the pre-mixing vessel 105 (block 2130) optionally with a portion of the humectant hexylene glycol (block 2135) and then the homogenization rate of the homogenizer 110 is set and begun (block 2140). In the present example, the homogenizer rate is set to 7500 revolutions per minute to provide a high shear homogenization. After beginning homogenization of the alcohol, the hydroxypropyl cellulose is rapidly added to the pre-mixing vessel 105 (block 2150). In particular, the hydroxypropyl cellulose may be added in less than 2 minutes or any range therein, in some cases, in less than 1 minute and, in some cases, in about 30 seconds. In some embodiments, at least one humectant, such as hexylene glycol, is added with the hydroxypropyl cellulose. For example, in some embodiments, a portion of the total humectant in the gel is added in the first excipient mixture while the remaining humectant is added with the second excipient composition. Any suitable amount of humectant may be added to the first excipient composition, but in some embodiments, the amount of humectant included in the first composition is that which is needed to swell the viscosity increasing agent.

After the hydroxypropyl cellulose is added to the pre-mixing vessel 105, the homogenization rate is reduced and the mixture is pumped through the peristaltic pump 155 to the mixing vessel 160 (block 2160) at a rate of at least 250 mL/min to avoid gelation during the transfer process. In particular, the mixture may be pumped at a rate of 500 mL/min. The mixing vessel 160 is set to mix the contents with a mixer speed of 10 to 50 RPM, and in particular at about 40 rpm. In the present example, the homogenizer rate is reduced to 4000 revolutions per minute. After transferring the mixed ethyl alcohol and hydroxypropyl cellulose to the mixing vessel 160, the homogenizer rate may be reset to the higher rate and the process begun again if more batches of material are required (block 2170). In the present example, the operations of block 2100 through 2170 are repeated three times. The pre-mixing vessel 105 is then rinsed with alcohol for 5 minutes and the contents transferred to the mixing vessel 160 through the peristaltic pump 155 at a flow rate of 500 mL/min (block 2175). Excipients and solvents are dosed either manually or through automated methods.

When the pre-mixing vessel 105 has been rinsed and transferred to the mixing vessel 106, the mixing vessel 160 mix rate is increased to about 45 RPM and the contents mixed for about 45 minutes (block 2180). Every 10 to 20 minutes or any range therein (block 2200), the contents of the mixing vessel 160 are recirculated through the valve 165, the in-line homogenizer 190, the valve 240 and optionally, the in-line analysis equipment 245 (block 2190) for about 3 minutes but not so long as to cause an undesirable temperature increase resulting from the high shear homogenization.

In block 2210, the pre-mixing of the API begins by adding the humectant hexylene glycol (in which in some embodiments, the remaining portion of the humectant is added—for example, one half of the total humectant concentration may optionally have been included in the first excipient composition (block 2135)) and ST-cyclomethicone-5 to the pre-mixing vessel 105. The homogenization rate of the homogenizer 110 is set and begun (block 2220). In the present example, the homogenizer rate is set to 4000 revolutions per minute. The materials are homogenized for about 5 minutes and the API (in this example, Nitricil™, a nitric oxide-releasing co-condensed silica) is added to the pre-mixing vessel 105 (block 2230). The homogenizer rate is reduced to 2500 revolutions per minute and the contents of the pre-mixing vessel 105 homogenized for about 10 minutes. The mixture in the pre-mixing vessel 105 is then pumped through the peristaltic pump 155 to the mixing vessel 160 (block 2240), for example at a rate of 500 mL/min. The pre-mixing vessel 105 is then rinsed with ethyl alcohol for about 5 minutes at a homogenization rate of 4000 revolutions per minute (blocks 2260 and 2270). After 5 minutes, the rate of the homogenizer 110 is reduced to 2500 revolutions per minute and the contents transferred to the mixing vessel 160 through the peristaltic pump 155, for example at a rate of 500 mL/min (block 2270). The combined contents of the mixing vessel 160 are mixed at a mixing rate of about 45 RPM for about an additional 90 minutes (block 2280). The mixed material may then be stored in any suitable container that avoids contact with moisture or may be pumped to a packaging system as described herein.

As will be appreciated by one of skill in the art in light of the present disclosure, the step/operations illustrated in may be carried out of sequence or concurrently or steps/operations may be combined while still falling within the scope of the present inventive concept. For example, if multiple rotor/stator homogenizing vessels are utilized what is illustrated in the Figures as a sequence of steps may be carried out simultaneously. Furthermore, operations which are illustrated as batch operations could be modified to provide continuous process operations. Accordingly, the flowchart illustrations should not be construed as limiting the scope of the present invention.

Figure 4A:
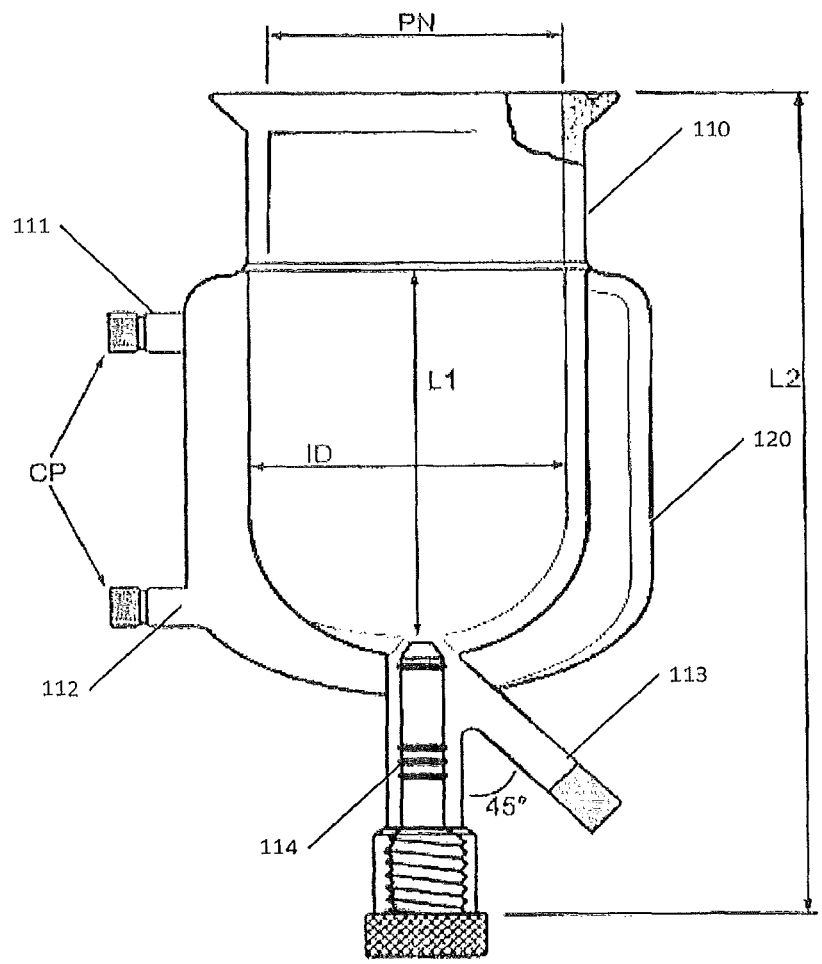
FIGS. 4A through 4C are drawings of a rotor-stator homogenizer according to some embodiments of the present inventive concept.
Figure 4B:
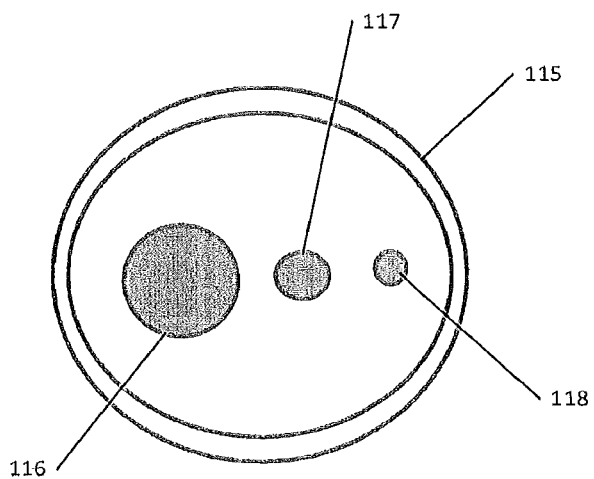
Figure 4C:
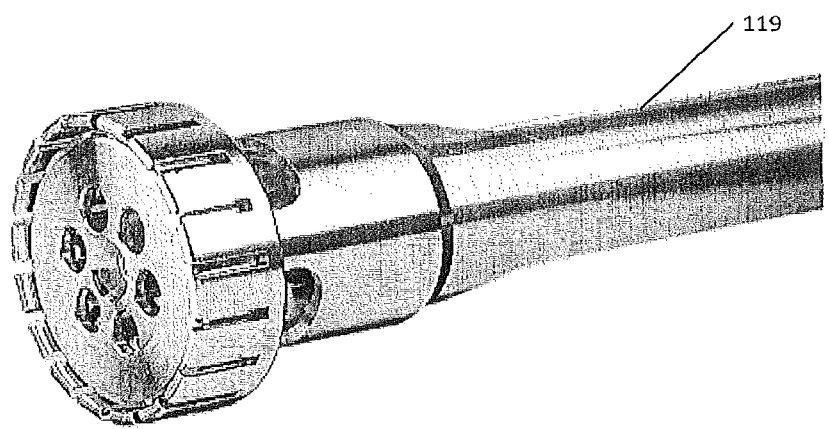

FIG. 4A is a cross section drawing of a pre-mixing vessel 105 suitable for use in the system 100. FIG. 4B is a drawing of the lid and FIG. 4C is a drawing of the rotar-stator for the homogenizer 110. As seen in FIG. 4A, the pre-mixing vessel 105 includes a homogenizer vessel 110 with a jacket 120 for passing heating/cooling media around the homogenizer vessel 110. The heating/cooling media enters and exits the jacket 120 through the inlet/outlet ports 111, 112. The homogenizer vessel 110 has a drain port 113 with a drain valve 114 that is a zero clearance valve so as to not leave any dead space in the homogenizer vessel 110 where ingredients could collect. Furthermore, the drain port 113 and drain valve 114 are large enough to provide for the rapid removal of material from the pre-mixing vessel 105 and so that it will not clog with the gel. The pre-mixing vessel 105 may be made of any suitable material but, in some embodiments, it is made of glass.

FIG. 4B illustrates the lid 115 of the pre-mixing vessel 105. The lid 115 includes three openings 116, 117, 118 that may be sealed and allow access to the homogenizer vessel 110. The largest opening 116 is for the rotor/stator 119 of the homogenizer. The middle opening 117 is for the inert gas. The smallest opening is for a temperature probe 118. The rotor/stator 119 illustrated in FIG. 4C allows for a seal where the shaft goes through the lid 115.

In a particular embodiment, the dimension PN is 170 mm, L1 is 200 mm, ID is 170 mm and L2 is 300 mm. The drain valve 114 is 20 mm. The opening 116 is 30 mm in diameter, the opening 117 is 20 mm in diameter and the opening 118 is 8 mm in diameter. The rotor/stator 119 is model number T50 from IKA-Werk. The use of the rotor/stator 119 allows for the placement of the opening 116 centered or off center in the lid 115.

While embodiments of the present inventive subject matter have been described with reference to particular configurations of a processing system and specific processing conditions variations to these systems and conditions may be made while still falling within the scope of the present inventive subject matter. For example, the processing system may include solid powder metering systems for raw materials, such as the Klucel and the API. Similarly, additional systems could be incorporated to prevent oxidation of the materials. For example, processing could be carried out under vacuum to remove oxygen and carbon dioxide, solutions could be degassed via vacuum or bubbling, the materials could be protected from light (e.g. if a nitrosothiol NO releasing donor is utilized) or light could be used to either photo-age the topical gel or eliminate photodecomposition of the topical gel or its components.

Packaging and Delivery of Topical Compositions

Returning to FIG. 1, also illustrated is a packaging system 300. As seen in FIG. 1, the packaging system 300 includes a hopper 310 for receiving the product to be packaged and a tube filler 320, such as an Arencomatic 1000 from Norden, for taking the product from the hopper 310, dispensing the product into a tube and sealing the tube. Argon gas is provided in the hopper 310 and to the tube filler 320 with the rate of flow being controlled by the tube filler 320 or a flow meter 330. A blanket of argon gas is provided in the hopper 310 and the hopper 310 filled from the bottom so that the product is not exposed to moisture in the air. The tube filler 320 fills preformed tubes with argon gas and then fills the tubes from the bottom to displace the gas and, thereby, reduce the likelihood that the product will be exposed to moisture.

In some embodiments, a nitric oxide-releasing topical therapeutic may be provided in sealed single dose tubes (e.g., 2 g tubes) that are oxygen impermeable to prevent moisture from reaching the topical therapeutic and causing release of the nitric oxide. The patient would then puncture the tube at the time of application and apply the product to their skin. The product could also be refrigerated until use to thereby further reduce the likelihood of premature release of the nitric oxide.

In addition to being oxygen impermeable, the coatings and adhesives of the tubes should not contaminate the topical gel in the tubes. In particular, the adhesive at the crimped end of the tube should not contain a cold seal. Adhesives such as Darex™ and related synthetic rubber and latex compounds, which could have an adverse reaction and subsequently could contaminate the topical gel such as initiating release of nitric oxide, changing the color of the gel or other undesirable result. In some embodiments, packaged nitric oxide-releasing topical gels may be provided with a shelf life of at least about one week.

In further embodiments, the packaged nitric oxide-releasing topical gels have a shelf life of at least about four weeks, at least about 12 weeks, at least about 26 weeks, or at least about 52 weeks. In still further embodiments, the packaged nitric oxide-releasing topical gels have a shelf life of from at least 12 to at least 104 weeks, or any range therein. As used herein, the term "shelf life" refers to the length of time a product (i.e., a topical gel of the present invention) maintains the ability to release a therapeutically effective amount of nitric oxide in an unopened package stored under recommended storage conditions. The shelf life may, for example, be evidenced by the "use by" or "best if used by" date for the product, the manufacturer's expiration date of the product and/or the actual product characteristics after the specified period of time. Accordingly, the term "shelf life" as used herein should be construed as including both an "actual" shelf life of the product and a "predicted" shelf life of the product unless stated otherwise. As one skilled in the art will recognize, the rate of release of nitric oxide in a topical gel under packaged and/or stored conditions may be different (i e, faster or slower) than the rate of release of nitric oxide when the topical gel is in use. In certain embodiments, the rate of release of nitric oxide may be faster when a topical gel is in use compared to the rate of release of nitric oxide when the topical gel was packaged and/or stored.

In some embodiments, the shelf life of the product is the time that the product maintains the ability to release at least 50% of the initial amount of nitric oxide that the product may release when packaged. In further embodiments, the shelf life of the product is the time that the product maintains the ability to release at least 70%, at least 80%, at least 90%, at least 95%, or at least 98% of the initial amount of nitric oxide that the product may release when packaged. In some embodiments, the recommended storage conditions are room temperature. In some embodiments, the recommended storage conditions are refrigerated storage conditions. In particular embodiments, the refrigerated storage conditions are between 1° C.-12° C., or any range therein.

Further embodiments may provide packaged nitric oxide-releasing topical gels that have a useful life of at least about 7 days after opening the package. In further embodiments, the useful life is at least about 30 days, at least about 60 days or at least about 90 days. In still further embodiments, the packaged nitric oxide-releasing topical gels have a useful life of from at least about 60 days to at least about 730 days. As used herein, the term "useful life" refers to the length of time that the product maintains the ability to release a therapeutically effective amount of nitric oxide from an opened packaged when applied as recommended and when stored under recommended storage conditions. The useful life may, for example, be evidenced by the manufacturer's recommended time to dispose of the product after opening or measurements of the products characteristics after opening.

Accordingly, the term "useful life" as used herein should be construed as including both an "actual" useful life of the product or a "predicted" useful life of the product unless stated otherwise. In some embodiments, the useful life of the product is the time that the product maintains the ability to release at least 50% of the initial amount nitric oxide that the product may release when the package is opened. In further embodiments, the shelf life of the product is the time that the product maintains the ability to release at least 70%, at least 80%, at least 90%, at least 95%, or at least 98% of the initial amount nitric oxide that the product may release when the package is opened. In some embodiments, the recommended storage conditions after opening are room temperature. In particular embodiments, the recommended storage conditions after opening are refrigerated conditions.

Methods of Using Anhydrous Topical Compositions

A composition described herein may be used to treat a dermatological ailment. For example, a composition of the present invention may be used to treat acne. In certain embodiments, the composition comprises at least one API, such as a NO-releasing API. In other embodiments, the composition comprises a vehicle and thus does not comprise an API. A composition described herein may be applied to the skin at a concentration sufficient to treat a dermatological ailment such as acne. As such, in some embodiments, a topical composition described herein may decrease, eliminate or prevent acne, decrease abnormal keratinization, reduce microbial colonization, reduce inflammation and/or decrease sebum production. Decrease of acne may be detected by a visual reduction in the amount or severity of the acne and/or by decrease in pain or discomfort associated with the acne, as identified by the subject.

In particular embodiments of the present invention, a topical composition described herein is non-drying and/or non-irritating to the skin of a subject. Dryness and/or irritation of the skin may be detected visually and/or as identified by a subject.

In some embodiments, an anhydrous topical composition according to embodiments of the invention is applied topically to the skin of the subject. Any portion of the subject's skin may be treated. However, in some embodiments, the subject's face is treated by a method described herein. Furthermore, in some embodiments, the subject's trunk is treated by a method described herein. The subject may have acne or a pharmaceutical composition described herein may be used to prevent acne from forming.

Subjects suitable to be treated with a method of the invention include, but are not limited to, avian and mammalian subjects. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects of both genders and at any stage of development (i.e., neonate, infant, juvenile, adolescent, adult) may be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The invention may also be carried out on animal subjects, particularly mammalian subjects such as mice, rats, dogs, cats, livestock and horses for veterinary purposes, and for drug screening and drug development purposes.

In some embodiments, a method of treating acne, decreasing abnormal keratinization, reducing microbial colonization, reducing inflammation and/or decreasing sebum production may include using a method described herein in combination with another therapeutic regimen and/or in combination with another API, such as those that have antimicrobial, anti-inflammatory, pain-relieving, immunosuppressant, vasodilating properties, and/or anti-acne properties. For example, other anti-acne agents such as retenoids, may be used in conjunction (prior, concurrently or after) with the application of the nitric oxide. As such, in some embodiments of the invention, a patient may be treated with nitric oxide, at least one NO releasing compound and/or a composition described herein in combination with an additional therapeutic agent when the additional therapeutic agent is not in the same composition. For example, in some embodiments, an additional therapeutic agent may be administered (e.g., topically, systemically, parenterally, orally, buccally, subcutaneously, via inhalation, intratracheally, surgically, transdermally, etc.), either concurrently and/or sequentially with application of nitric oxide, at least one nitric oxide source and/or a pharmaceutically acceptable composition that includes at least one nitric oxide source.

In some embodiments of the invention, a pharmaceutically acceptable composition described herein may be administered to the skin via spray delivery. A non-aqueous delivery propellant may be used for water sensitive NO-releasing compounds including diazeniumdiolate-modified compounds. Further, in some embodiments, particular components of the medicaments may be separated at some point prior to application of the medicament. For example, a water reactive NO-releasing compound may be stored separately from an aqueous component or propellant until application (e.g., via spraying or applying a gel). In some embodiments, the NO-releasing compounds may be combined with an aqueous constituent prior to application or the NO-releasing compounds and an aqueous constituent may be applied to the skin sequentially.

While some embodiments of the present inventive concept may be suitable for treating acne so as to moderate production of sebum, moderate abnormal keratinization, reduce inflammation and/or reduce microbial colonization, some embodiments may promote healing of a wound associated with the dermatological condition, affect a biofilm associated with the dermatological condition and/or reduce scarring from a wound associated with the dermatological condition. Additionally, embodiments of the present inventive concept may also treat the dermatological condition without significant side effects.

Accordingly, particular embodiments of the present inventive concept provide a method of treating a dermatological condition by topically administering a nitric oxide releasing topical composition in an amount effective to actively promote healing of a wound associated with the dermatological condition. Some embodiments provide a method of treating a dermatological condition by topically administering a nitric oxide releasing composition in an amount effective to affect a biofilm associated with the dermatological condition. Still further embodiments provide a method of treating a dermatological condition by topically administering a nitric oxide releasing composition in an amount effective to reduce scarring from a wound associated with the dermatological condition. Some embodiments provide a method of treating a dermatological condition by topically administering a nitric oxide releasing composition in an amount effective to treat the dermatological condition without significant side effects.

Wound healing may be effected through prolonged low concentrations of nitric oxide administration whereby nitric oxide acts as a signaling molecule in a number of wound healing cascades. An intermediate NO-releasing composition may mitigate the inflammatory phase. High levels of NO-released may be necessary to effect antimicrobial activity, using the rapid burst of nitric oxide to kill microorganisms through oxidative/nitrosative intermediates. In some embodiments, provided is a kit for the topical treatment of dermatological ailments that includes at least one composition that includes at least one viscosity increasing agent, at least one organic solvent, at least one humectant and at least one water repellant. In some embodiments, a kit includes a first composition that releases low concentrations of nitric oxide; and a second composition that releases a higher level of nitric oxide. Additional APIs may be included in some or all of the compositions to increase efficacy.

While embodiments of the present invention have been described as providing a topical composition that includes an API, in some embodiments, a topical composition according to the present invention may be used to treat a condition and, in particular, a dermatological condition as described herein, such as acne, without the inclusion of an API. In such embodiments of the present invention, the "vehicle" may be used to treat the dermatological condition. Accordingly, therapeutic applications of a topical composition of the present invention include application of a topical composition with and/or without an API included in the topical composition.

EXAMPLES

Example 1: Examples of Topical Gels

TABLE 1

Nitricil ™ Gel, 0.2%

| Component | Supplier | Quality Standard | Function | % w/w |
|---|---|---|---|---|
| Ethyl alcohol, anhydrous, 200 proof, USP or Isopropyl alcohol, USP | Koptec or BDH | USP | Solvent | 85.3 |
| Hexylene glycol, 99% | Fluka/ Sigma | Reagent | Co-solvent/ Humectant | 10.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 2.0 |
| Nitricil ™ | Novan | N/A | API | 0.2 |
| Total | | | | 100.0 |

TABLE 2

Nitricil ™ Gel, 0.5%

| Component | Supplier | Quality Standard | Function | % w/w |
|---|---|---|---|---|
| Ethyl alcohol, anhydrous, 200 proof, USP or Isopropyl alcohol, USP | Koptec or BDH | USP | Solvent | 85.0 |
| Hexylene glycol, 99% | Fluka/ Sigma | Reagent | Co-solvent/ Humectant | 10.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 2.0 |
| Nitricil ™ | Novan | N/A | API | 0.5 |
| Total | | | | 100.0 |

TABLE 3

Nitricil ™ Gel, 1%

| Component | Supplier | Quality Standard | Function | % w/w |
|---|---|---|---|---|
| Ethyl alcohol, anhydrous, 200 proof, USP or Isopropyl alcohol, USP | Koptec or BDH | USP | Solvent | 84.5 |
| Hexylene glycol, 99% | Fluka/ Sigma | Reagent | Co-solvent/ Humectant | 10.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 2.0 |
| Nitricil ™ | Novan | N/A | API | 1.0 |
| Total | | | | 100.0 |

TABLE 4

Nitricil ™ Gel, 2%

| Component | Supplier | Quality Standard | Function | % w/w |
|---|---|---|---|---|
| Ethyl alcohol, anhydrous, 200 proof, USP or Isopropyl alcohol, USP | Koptec or BDH | USP | Solvent | 83.5 |
| Hexylene glycol, 99% | Fluka/ Sigma | Reagent | Co-solvent/ Humectant | 10.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 2.0 |
| Nitricil ™ | Novan | N/A | API | 2.0 |
| Total | | | | 100.0 |

TABLE 5

Nitricil™ Gel, 3%

| Component | Supplier | Quality Standard | Function | % w/w |
|---|---|---|---|---|
| Ethyl alcohol, anhydrous, 200 proof, USP or Isopropyl alcohol, USP | Koptec or BDH | USP | Solvent | 82.5 |
| Hexylene glycol, 99% | Fluka/Sigma | Reagent | Co-solvent/Humectant | 10.0 |
| Nitricil™ | Novan | N/A | API | 3.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 2.0 |
| Total | | | | 100.0 |

TABLE 6

Nitricil™ Gel, 4%

| Component | Supplier | Quality Standard | Function | % w/w |
|---|---|---|---|---|
| Ethyl alcohol, anhydrous, 200 proof, USP or Isopropyl alcohol, USP | Koptec or BDH | USP | Solvent | 81.5 |
| Hexylene glycol, 99% | Fluka/Sigma | Reagent | Co-solvent/Humectant | 10.0 |
| Nitricil™ | Novan | N/A | API | 4.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 2.0 |
| Total | | | | 100.0 |

TABLE 7

Nitricil™ Gel, 5%

| Component | Supplier | Quality Standard | Function | % w/w |
|---|---|---|---|---|
| Ethyl alcohol, anhydrous, 200 proof, USP or Isopropyl alcohol, USP | Koptec or BDH | USP | Solvent | 80.5 |
| Hexylene glycol, 99% | Fluka/Sigma | Reagent | Co-solvent/Humectant | 10.0 |
| Nitricil™ | Novan | N/A | API | 5.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 2.0 |
| Total | | | | 100.0 |

TABLE 8

Nitricil™ Gel, 6%

| Component | Supplier | Quality Standard | Function | % w/w |
|---|---|---|---|---|
| Isopropyl alcohol, USP | Koptec or BDH | USP | Solvent | 80.5 |
| Hexylene glycol, 99% | Fluka/Sigma | Reagent | Co-solvent/Humectant | 10.0 |
| Nitricil™ | Novan | N/A | API | 6.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 1.0 |
| Total | | | | 100.0 |

TABLE 9

Nitricil™ Gel, 12%

| Component | Supplier | Quality Standard | Function | % w/w |
|---|---|---|---|---|
| Isopropyl alcohol, USP | Koptec or BDH | USP | Solvent | 74.5 |
| Hexylene glycol, 99% | Fluka/Sigma | Reagent | Co-solvent/Humectant | 10.0 |
| Nitricil™ | Novan | N/A | API | 12.0 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 1.0 |
| Total | | | | 100.0 |

TABLE 10

Nitricil™ Gel, 20%

| Component | Supplier | Quality Standard | Function | % w/w |
|---|---|---|---|---|
| Isopropyl alcohol, USP | Koptec or BDH | USP | Solvent | 66.5 |
| Hexylene glycol, 99% | Fluka/Sigma | Reagent | Co-solvent/Humectant | 10.0 |
| Nitricil™ | Novan | N/A | API | 20 |
| Cyclomethicone, NF ST-Cyclomethicone-5 | Dow Corning | NF | Water-repelling agent | 2.5 |
| Hydroxypropyl cellulose, NF Klucel MF Pharm | Ashland | NF | Viscosity-modifying agent | 1.0 |
| Total | | | | 100.0 |

TABLE 11

Nitricil™ Gel, 30%

| Component | Supplier | Quality Standard | Function | % w/w |
|---|---|---|---|---|
| Isopropyl alcohol, USP | Koptec or BDH | USP | Solvent | 56.5 |
| Hexylene glycol, 99% | Fluka/Sigma | Reagent | Co-solvent/Humectant | 10.0 |
| Nitricil™ | Novan | N/A | API | 30.0 |
| Cyclomethicone, NF | Dow | NF | Water-repelling | 2.5 |

TABLE 11-continued

Nitricil™ Gel, 30%

| Component | Supplier | Quality Standard | Function | % w/w |
|---|---|---|---|---|
| ST-Cyclomethicone-5 | Corning | | agent | |
| Hydroxypropyl cellulose, NF Klucel MF Pharm | Ashland | NF | Viscosity-modifying agent | 1.0 |
| | | | Total | 100.0 |

TABLE 12

Placebo Gel

| Component | Supplier | Quality Standard | Function | % w/w |
|---|---|---|---|---|
| Ethyl alcohol, anhydrous, 200 proof USP or Isopropyl alcohol, USP | Koptec or BDH | USP | Solvent | 85.5 |
| Hexylene glycol, 99% | Fluka/Sigma | Reagent | Co-solvent/Humectant | 10.0 |
| Cyclomethicone, NF ST-Cyclomethicone-5 | Dow Corning | NF | Water-repelling agent | 2.5 |

TABLE 12-continued

Placebo Gel

| Component | Supplier | Quality Standard | Function | % w/w |
|---|---|---|---|---|
| Hydroxypropyl cellulose, NF Klucel MF Pharm | Ashland | NF | Viscosity-modifying agent | 2.0 |
| | | | Total | 100.0 |

Example 2: NO-Releasing Topical Gels *P. Acne* Time Kill

A 2% API loaded anhydrous gel of a specific embodiment described herein, wherein the API is a nitric oxide releasing macromolecule, was tested for efficacy in the reduction of *P. acnes*, using ASTM E-2315. In this test, *Propionibacterium acnes* ATCC 6919 ($10^6$ CFU/ml) were incubated with 250 mg of gel vehicle or 250 mg of active gel containing Nitricil™ (4 mg/ml) in 37° C. phosphate buffered saline (PBS). After 30 minutes, 2 hours, and 4 hours of incubation, aliquots from each tube were removed, neutralized with letheen broth, serially diluted, and plated to obtain viable colony counts.

TABLE 13

Control Blank

| Control | Time, hrs 0 | 0.5 | 1 | 2 | Control | Time, hrs 0 | 0.5 | 1 | 2 |
|---|---|---|---|---|---|---|---|---|---|
| 1 | 2.10E+06 | 1.60E+06 | 2.00E+06 | 1.60E+06 | 1 | .32 | .20 | .30 | .20 |
| 2 | 2.20E+06 | 1.60E+06 | 1.80E+06 | 1.90E+06 | 2 | .34 | .20 | .26 | .28 |
| Average | 2.15E+06 | 1.60E+06 | 1.90E+06 | 1.75E+06 | Average | .33 | .20 | .28 | .24 |
| STDERR | 3.54E+04 | 0.00E+00 | 7.07E+04 | 1.06E+05 | STDERR | .01 | .00 | .02 | .03 |
| % Reduction vs ctrl | 0 | 26 | 12 | 19 | Log Reduction vs Ctrl | .00 | .13 | .05 | .09 |

TABLE 14

Gel vehicle by itself

| Gel Vehicle | Time, hrs 0 | 0.5 | 1 | 2 | Gel Vehicle | Time, hrs 0 | 0.5 | 1 | 2 |
|---|---|---|---|---|---|---|---|---|---|
| 1 | 2.30E+06 | 1.80E+06 | 1.80E+06 | 2.90E+05 | 1 | .36 | .26 | .26 | .46 |
| 2 | 2.10E+06 | 2.00E+06 | 2.10E+06 | 3.30E+05 | 2 | .32 | .30 | .32 | .52 |
| Average | 2.20E+06 | 1.90E+06 | 1.95E+06 | 3.10E+05 | Average | .34 | .28 | .29 | .49 |
| STDERR | 7.07E+04 | 7.07E+04 | 1.06E+05 | 1.41E+04 | STDERR | .01 | .02 | .02 | .02 |
| % Reduction vs ctrl | −2 | 12 | 9 | 86 | Log Reduction vs Ctrl | 0.01 | .05 | .04 | .84 |

TABLE 15

Gel vehicle with Nitricil™

| 2% Nitricil™ Gel 11-9-37 | Time, hrs 0 | 0.5 | 1 | 2 | 2% Nitricil™ Gel 11-9-37 | Time, hrs 0 | 0.5 | 1 | 2 |
|---|---|---|---|---|---|---|---|---|---|
| 1 | 1.90E+06 | 2.10E+03 | 1.00E+01 | 1.00E+01 | 1 | .28 | .32 | .00 | .00 |
| 2 | 1.80E+06 | 2.10E+03 | 1.00E+01 | 1.00E+01 | 2 | .26 | .32 | .00 | .00 |

TABLE 15-continued

Gel vehicle with Nitricil™

| 2% Nitricil™ Gel 11-9-37 | Time, hrs | | | | 2% Nitricil™ Gel 11-9-37 | Time, hrs | | | |
|---|---|---|---|---|---|---|---|---|---|
| | 0 | 0.5 | 1 | 2 | | 0 | 0.5 | 1 | 2 |
| Average | 1.85E+06 | 2.10E+03 | 1.00E+01 | 1.00E+01 | Average | .27 | .32 | .00 | .00 |
| STDERR | 3.54E+04 | 0.00E+00 | 0.00E+00 | 0.00E+00 | STDERR | .01 | .00 | .00 | .00 |
| % Reduction vs ctrl | 14 | 99.90 | 99.9995 | 99.9995 | Log Reduction vs Ctrl | .07 | 01 | .33 | .33 |

TABLE 16

Summary of Data

| % Reduction | Time, hrs | | | | Log Reduction | Time, hrs | | | |
|---|---|---|---|---|---|---|---|---|---|
| | 0 | 0.5 | 1 | 2 | | 0 | 0.5 | 1 | 2 |
| Control | | 6 | 12 | 19 | Control | .00 | .13 | .05 | .09 |
| Gel Vehicle | 2 | 2 | 9 | 86 | Gel Vehicle | 0.01 | .05 | .04 | .84 |
| 2% Nitricil™ Gel | 4 | 9.90 | >99.999 | >99.999 | 2% Nitricil™ Gel | .07 | .01 | 5.33 | 5.33 |

Figure 5:
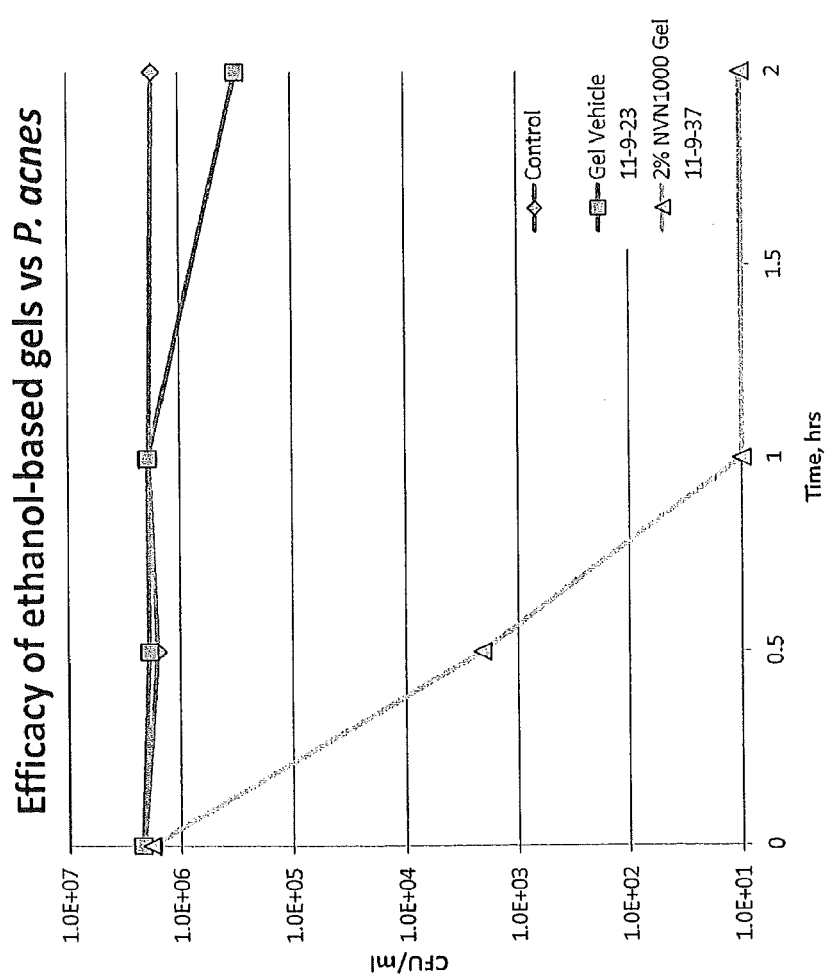
FIG. 5 shows the reduction in $P.\ acnes$ for a control blank, a gel vehicle and a composition according to an embodiment of the invention.

The data in Tables 13-16 is also shown graphically in FIG. 5. As can be seen from Table 16 and FIG. 5, a NO-releasing composition according to an embodiment of the invention can be effective to kill *P. acnes*.

Example 3

Figure 6:
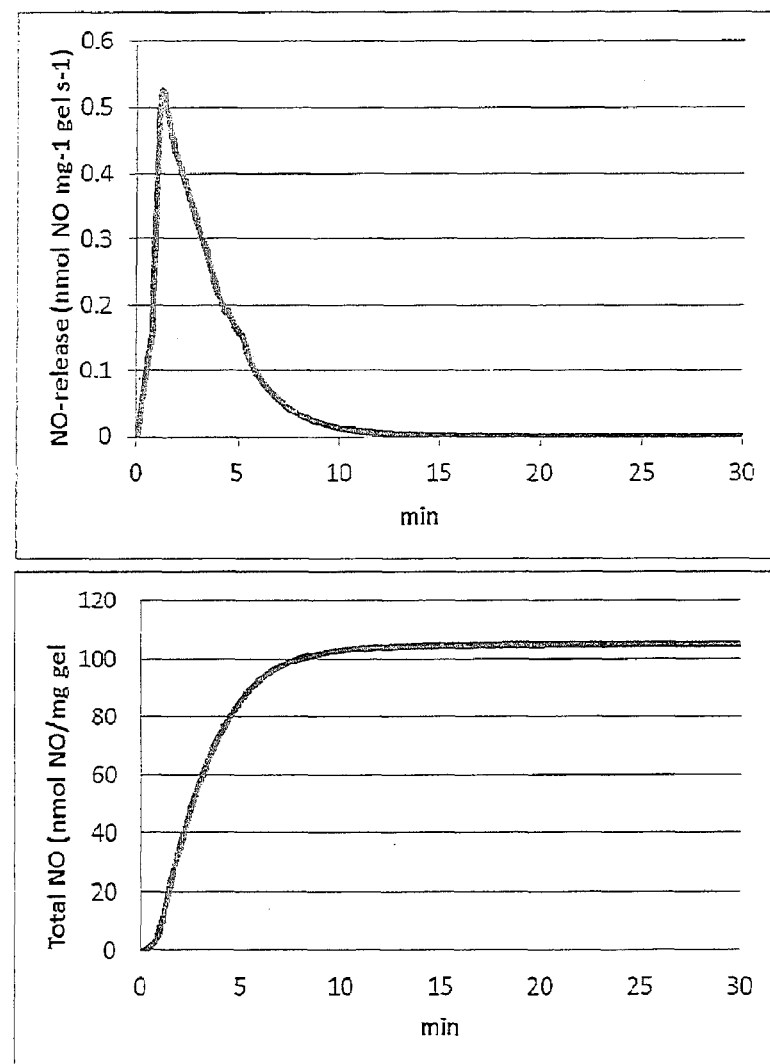
FIG. 6 shows the nitric oxide release detected via chemiluminescence in real time from a 2% API loaded anhydrous gel, wherein the API is a nitric oxide releasing macromolecule, when placed in phosphate buffered saline at a representative skin pH of 6.0. Additionally, the total nitric oxide release from the anhydrous gel in nmol NO/mg gel is shown, demonstrating complete release in under 30 minutes.

The NO release profile for 2% Nitricil™ in anhydrous gel, as tested in Example 1 and made by the process described herein, is shown in FIG. 6. At a pH of 6.0 that may be encountered in the stratum corneum, the maximum flux of nitric oxide exceeded 0.5 nmol NO per mg gel per second and a half-life of about 160 seconds.

Example 4

Figure 7:
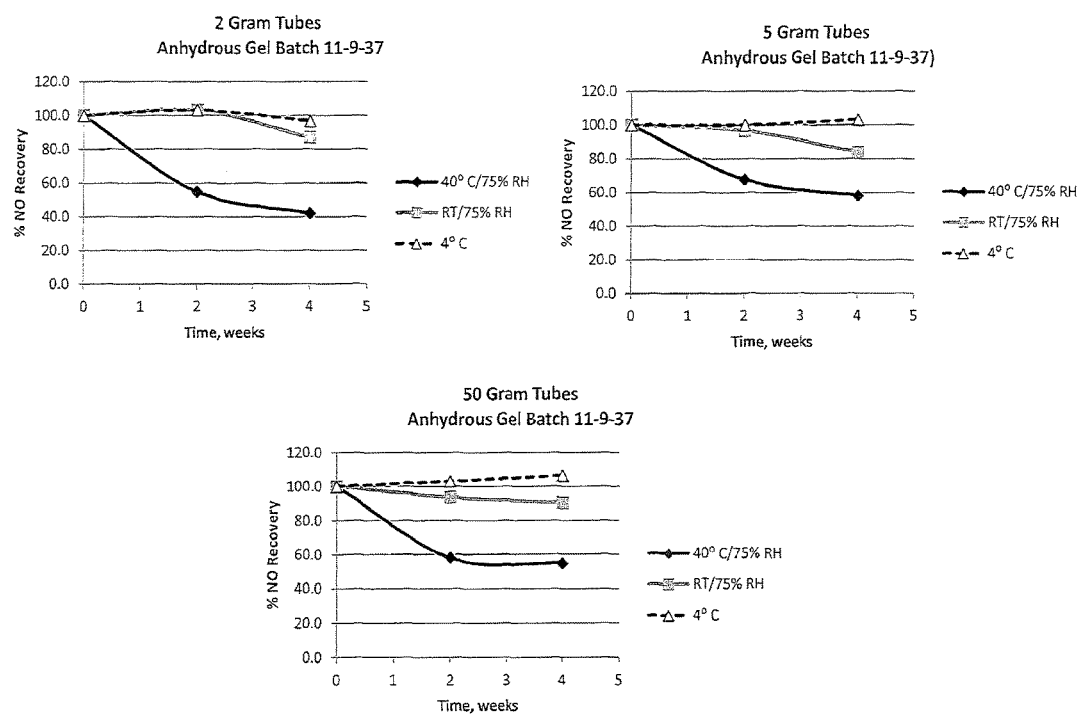
FIG. 7 shows the stability of a 2% API loaded anhydrous gel, wherein the API is a nitric oxide releasing macromolecule, packaged in various sized aluminum tubes and maintained in the following conditions: refrigerated (4° C.), room temperature with 75% relative humidity, and 40° C. with 75% relative humidity. Percent NO recovery values were measured by the total NO release detected via chemiluminescence at each time point and presented as a percentage of the nitric oxide loading at time=0.

Stability data for 2% Nitricil™ in anhydrous gel, as tested in Example 1 and made by the process described herein, are shown in FIG. 7

Example 5—Macromolecular Nitric Oxide Releasing Compound

A nitric oxide releasing macromolecular compound comprising MAP3 was fabricated as described in United States Patent Application Publication No. 2009/0214618 and in PCT Patent Application Number PCT/US12/22048, filed Jan. 20, 2012, entitled "Temperature Controlled Sol-Gel Co-Condensation," the disclosures of which are incorporated herein by reference as if set forth in their entirety. The resulting macromolecular particles were ball milled to provide an average particle size of from 8 to 10 μm to provide an active pharmaceutical ingredient (API).

Example 6—Topical Gel with Active Pharmaceutical Ingredient

Topical gel incorporating the API of Example 5 ("Active") was fabricated as described in U.S. Provisional Patent Application Ser. No. 61/504,628 entitled "Topical Compositions and Methods of Using Same to Treat Acne," and U.S. Provisional Patent Application Ser. No. 61/504,626, entitled "Methods of Manufacturing Topical Compositions and Apparatus for Same," both of which were filed Jul. 5, 2011 and are incorporated herein as if set forth in their entirety. In particular, the Active had the formulation of:

TABLE 17

Active Gel

| Component | Quality Standard | Function | % w/w |
|---|---|---|---|
| Ethyl alcohol, anhydrous, 200 proof, USP | USP | Solvent | 83.5 |
| Hexylene glycol, 99% | Reagent | Co-solvent/ Humectant | 10.0 |
| Cyclomethicone, NF ST-Cyclomethicone-5 | NF | Water-repelling agent | 2.5 |
| Hydroxypropyl cellulose, NF Klucel MF Pharm | NF | Viscosity-modifying agent | 2.0 |
| Nitricil™ | N/A | API | 2.0 |

Example 7—Topical Gel with Masking Agent

Topical gel incorporating titanium dioxide as a masking agent ("Vehicle") was fabricated as described in U.S. Provisional Patent Application Ser. No. 61/504,628 entitled "Topical Compositions and Methods of Using Same to Treat Acne," and U.S. Provisional Patent Application Ser. No. 61/504,626, entitled "Methods of Manufacturing Topical Compositions and Apparatus for Same," both of which were filed Jul. 5, 2011 and are incorporated herein as if set forth in their entirety. In particular, the Vehicle had the formulation of:

TABLE 18

| Vehicle Gel | | | |
|---|---|---|---|
| Component | Quality Standard | Function | % w/w |
| Ethyl alcohol, anhydrous, 200 proof, USP | USP | Solvent | 85.45 |
| Hexylene glycol, 99% | Reagent | Co-solvent/Humectant | 10.0 |
| Cyclomethicone, NF ST-Cyclomethicone-5 | NF | Water-repelling agent | 2.5 |
| Hydroxypropyl cellulose, NF Klucel MF Pharm | NF | Viscosity-modifying agent | 2.0 |
| Titanium dioxide | N/A | | 0.05 |

All clinical trial materials were packaged in single use 2 g tubes on an Arencomatic 1000 automated packaging system from Norden. The 2 g tubes were stored at 5° C. until dispensing to trial subjects. The tubes packaged into 2 week kits.

Example 8—Clinical Study Protocol

A single-center, double-blind, randomized, vehicle-controlled, parallel group study was conducted in 70 intent-to-treat (ITT) subjects with moderate to severe acne vulgaris. The study included male and female subjects between the ages of 12 and 40 (inclusive) with moderate to severe acne vulgaris, defined as at least 20 but no more than 40 inflammatory lesions (papules and pustules), 20 to 60 non-inflammatory lesions (open and closed comedones), no more than 2 nodules, and an Investigator Global severity Assessment of 3 or 4. Subjects who satisfied the entry criteria at the Baseline visit were randomized to either Active or Vehicle in a 1:1 ratio. Tolerability and safety assessments included cutaneous tolerability evaluation, physical exams, collection of vital signs, blood pressure monitoring, urine pregnancy tests (UPTs), blood methemoglobin monitoring and adverse event collection. Efficacy assessments included inflammatory and noninflammatory lesion counts and an Investigator global severity assessment (IGA). Subjects returned for post-baseline evaluation at Weeks 2, 4, 6 and 8. Of the 70 ITT subjects enrolled in the study, 60 subjects completed the study per the study protocol. The subjects were provided kits with a two week supply of the 2 g tubes at each visit and instructed to maintain the tubes under refrigerated conditions until use.

Example 9—Tolerability and Safety Results

Cutaneous tolerability results of the study are shown in Table 19 for the Active and Table 20 for the Vehicle.

TABLE 19

| Summary of Cutaneous Tolerability at Baseline and Week 8 - Active | | | | | | | | | |
|---|---|---|---|---|---|---|---|---|---|
| | Baseline Pre-Application | | | Maximum Severity | | | Week 8 | | |
| | Mild | Mod | Severe | Mild | Mod | Severe | Mild | Mod | Severe |
| Erythema | 1 (2.9)% | 0 | 0 | 4 (12.1)% | 2 (5.7%) | 0 | 1 (3.0)% | 0 | 0 |
| Scaling | 0 | 0 | 0 | 2 (5.7%) | 2 (5.7%) | 0 | 0 | 1 (3.0)% | 0 |
| Dryness | 0 | 0 | 0 | 0 | 0 | 0 | 0 | 0 | 0 |
| Itching | 3 (8.6%) | 2 (5.7%) | 0 | 4 (11.8%) | 2 (6.1%) | 0 | 2 (6.1%) | 2 (6.1%) | 0 |
| Burning/Stinging | 0 | 0 | 0 | 1 (3.0)% | 1 (3.0%) | 0 | 1 (3.0)% | 0 | 0 |

TABLE 20

| Summary of Cutaneous Tolerability at Baseline and Week 8 - Vehicle | | | | | | | | | |
|---|---|---|---|---|---|---|---|---|---|
| | Baseline Pre-Application | | | Maximum Severity | | | End of Treatment (Wk 8) | | |
| | Mild | Mod | Severe | Mild | Mod | Severe | Mild | Mod | Severe |
| Erythema | 1 (2.9)% | 0 | 0 | 2 (5.7%) | 0 | 0 | 0 | 0 | 0 |
| Scaling | 0 | 0 | 0 | 1 (2.9%) | 0 | 0 | 0 | 0 | 0 |
| Dryness | 0 | 0 | 0 | 0 | 0 | 0 | 0 | 0 | 0 |
| Itching | 6 (17.1%) | 1 (2.9%) | 0 | 1 (2.9%) | 0 | 0 | 0 | 0 | 0 |
| Burning/Stinging | 0 | 0 | 0 | 1 (2.9%) | 0 | 0 | 1 (3.6%) | 0 | 0 |

Methemoglobin results were obtained by pulse co-oximeter from Masimo. The results at baseline, 2 weeks and 8 weeks are shown in Table 21.

TABLE 21

Methemoglobin Levels as Measured by Pulse Co-Oximetry

|  | Baseline | 2 Weeks | 8 Weeks |
|---|---|---|---|
| Active | | | |
| N | 35 | 35 | 34 |
| Mean | 0.9 | 1.1 | 0.9 |
| STD | 0.3 | 0.3 | 0.3 |
| Vehicle | | | |
| N | 35 | 34 | 31 |
| Mean | 0.7 | 1.0 | 0.8 |
| STD | 0.3 | 0.3 | 0.4 |

As seen in Table 21, the methemoglobin levels for Active and Vehicle subjects were will within acceptable ranges and did not differ significantly.

Example 10—Shelf Life

Tubes of the clinical supplies were maintained under controlled conditions at 5° C. and periodically evaluated for nitric oxide content. Tubes were also maintained at a controlled storage facility at 5° C. by the packager/labeler that prepared the kits and evaluated for nitric oxide content. Unused materials distributed to and retrieved from the clinical study site in the Dominican Republic were also evaluated for nitric oxide content. The results of the evaluation for remaining nitric oxide are shown in Table 22.

TABLE 22

Shelf Life Stability of 2% Topical Gel in 2 gram Tubes

| Active Gel 5° C. | % Recovery vs Initial NO Loading | Relative Std Dev |
|---|---|---|
| 6 month Stability @ Storage Facility | 96.6% | N/A (n = 2) |
| Retained Clinical Materials | 100% | 0.5% (n = 3) |
| Material Retuned from Clinical Trial | 93.1% | 4.6% (n = 4) |

Example 11—NO Recovery Over Time

Figure 8:
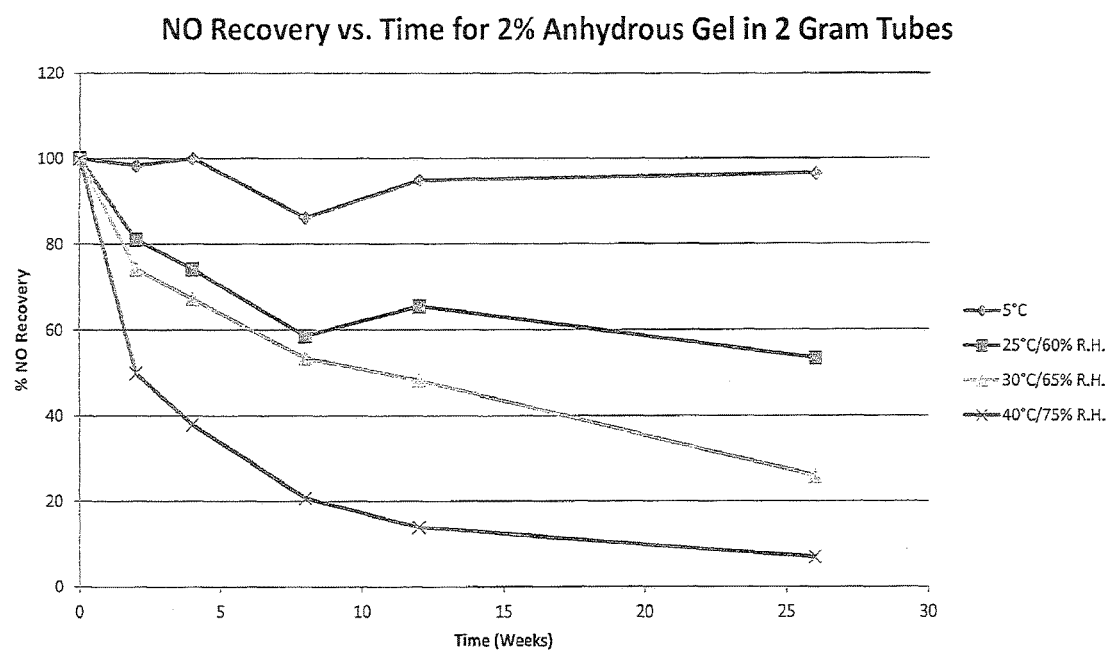
FIG. 8 shows a graph of nitric oxide recovery versus time for a 2% anhydrous gel in 2 gram tubes.

Tubes of a 2% anhydrous gel were stored at 5° C., 25° C./60% relative humidity (R.H.), 30° C./65% R.H., and 40° C./75% R.H. At 2, 4, 8, 12 and 16 weeks, the gel in the tubes was evaluated for nitric oxide content. FIG. 8 shows the nitric oxide recovery for the 2% anhydrous gels in 2 gram tubes over a time. The results of the stability study are provided in Table 23.

TABLE 23

Stability of 2% anhydrous gel at various temperatures over 26 weeks

| Temperature/ Relative Humidity | % NO Recovered at Week 2 | % NO Recovered at Week 4 | % NO Recovered at Week 8 | % NO Recovered at Week 12 | % NO Recovered at Week 26 |
|---|---|---|---|---|---|
| 5° C. | 98.27586 | 100 | 86.2069 | 94.82759 | 96.55172 |
| 25° C./60% R.H. | 81.03448 | 74.13793 | 58.62069 | 65.51724 | 53.44828 |
| 30° C./65% R.H. | 74.13793 | 67.24138 | 53.44828 | 48.27586 | 25.86207 |
| 40° C./75% R.H. | 50 | 37.93103 | 20.68966 | 13.7931 | 6.896552 |

Example 12—Activity of Vehicle for *P. Acnes* in Healthy Patients

Topical Gel Vehicle with titanium dioxide was produced as described in Example 7. Topical Gel Vehicle without titanium dioxide was produced as described in Example 7 except the titanium dioxide was replaced with additional ethyl alcohol. These formulations were evaluated to determine if the Vehicle in the clinical study had antimicrobial activity. A vehicle with antimicrobial activity could mask the effectiveness of an active ingredient in a clinical study.

Topical Gel Vehicle with titanium dioxide and Topical Gel Vehicle without titanium dioxide were evaluated in vivo to determine the effects on *P. acnes* and cutaneous tolerability. Thirty-one healthy adult males and females 18 years of age and older were enrolled in the study after meeting eligibility requirements at screening, 7-10 days prior to baseline. Subjects were carefully screened to ensure that none were using any prohibited topical or systemic antibiotics within 4 weeks prior to enrollment. The panelists were instructed not to use any antimicrobial topical products (e.g., soaps, medicated shampoos, acne preparations) during the study. The volunteers were selected for the study based on a high degree of fluorescence of the facial skin under a Wood's lamp indicating the presence of high levels of *P. acnes*. Baseline *P. acnes* counts were at least 10,000 colonies per $cm^2$ on the facial skin.

Subjects were treated for four weeks with either Topical Gel Vehicle with titanium dioxide or Topical Gel Vehicle without titanium dioxide. Each volunteer was treated once daily on the central forehead under supervision by a technician at the site beginning on the Thursday following acceptance into the study. Topical Gel Vehicle was also applied by the subjects (unsupervised) at home once daily on Saturdays and Sundays. At each visit, a sufficient amount of the test product (pea-sized amount) was applied and rubbed in for about 30 seconds.

Quantitative bacteriologic cultures were obtained from the test site at Baseline (0) and at Weeks 2 and 4. During the study, cutaneous tolerability assessments were made at Baseline and Weeks 1, 2, 3 and 4. Each of the local signs and symptoms, erythema, dryness, scaling, stinging/burning and itching were assessed on a four point scale where 0=none, 1=mild, 2=moderate, and 3=severe. Thirty-one patients were enrolled and 30 patients completed the study. One patient was discontinued prematurely by the Investigator for non-compliance.

Table 24 includes the *P. acnes* counts for the 4 week study. As seen in Table 24, neither of the formulations tested achieved significant reductions in *P. acnes*.

TABLE 24

|  | Total P. acnes Total P. acnes (Log/cm²) | | | |
| --- | --- | --- | --- | --- |
|  | Topical Gel Vehicle without titanium dioxide | | Topical Gel Vehicle with titanium dioxide | |
|  | Mean ± Std | over | Mean ± Std | over |
| Baseline | 6.75± | N/A | 6.72± | N/A |
| Week 2 | 6.66± | 0.0180 | 6.69± | 0.0000 |
| Week 4 | 6.64± | 0.0037 | 6.67± | 0.0000 |
|  | Net Change from Baseline | | | |
| Week 2 | −0.08 ± 0.12 | N/A | −0.05± | N/A |
| Week 4 | −0.11 ± 0.12 | N/A | −0.07± | N/A |

With regard to the cutaneous tolerability assessment, there was no erythema, scaling or itching observed/reported during the study with either formulation. There was only one report of mild (score=1) burning/stinging at Week 1 with the topical gel without titanium dioxide and one report of mild (score=1) dryness with the topical gel with titanium dioxide at Week 4.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed is:

1. An anhydrous composition consisting essentially of:
   hydroxypropyl cellulose at a concentration in a range of 0.5% to about 2% by weight of the anhydrous composition,
   ethanol or isopropyl alcohol at a concentration in a range of 45% to 90% by weight of the anhydrous composition,
   hexylene glycol at a concentration of about 10% by weight of the anhydrous composition,
   cyclomethicone at a concentration of about 2.5% by weight of the anhydrous composition, and
   a nitric oxide (NO)-releasing compound at a concentration in a range of 0.01% to 40% by weight of the anhydrous composition.

2. The anhydrous composition of claim 1, wherein the anhydrous composition comprises ethanol.

3. The anhydrous composition of claim 1, wherein the anhydrous composition comprises isopropyl alcohol.

4. The anhydrous composition of claim 1, wherein the NO-releasing compound is present in the anhydrous composition at a concentration in a range of 0.01% to 30% by weight of the anhydrous composition.

5. The anhydrous composition of claim 1, wherein the NO-releasing compound is present in the anhydrous composition at a concentration in a range of 0.01% to 2% by weight of the anhydrous composition.

6. The anhydrous composition of claim 1, wherein the hydroxypropyl cellulose is present in the anhydrous composition at a concentration in a range of 0.5% to about 1% by weight of the anhydrous composition.

7. The anhydrous composition of claim 1, wherein the hydroxypropyl cellulose is present in the anhydrous composition at a concentration of about 1% by weight of the anhydrous composition.

8. The anhydrous composition of claim 1, wherein the NO-releasing compound is present in the anhydrous composition at a concentration of about 1% by weight of the anhydrous composition.

9. The anhydrous composition of claim 1, wherein the NO-releasing compound is present in the anhydrous composition at a concentration of about 2% by weight of the anhydrous composition.

10. The anhydrous composition of claim 1, wherein the NO-releasing compound is present in the anhydrous composition at a concentration of about 4% by weight of the anhydrous composition.

11. The anhydrous composition of claim 1, wherein the NO-releasing compound is present in the anhydrous composition at a concentration of about 8% by weight of the anhydrous composition.

12. The anhydrous composition of claim 1, wherein the NO-releasing compound is present in the anhydrous composition at a concentration of about 12% by weight of the anhydrous composition.

13. The anhydrous composition of claim 1, wherein the NO-releasing compound is present in the anhydrous composition at a concentration of about 16% by weight of the anhydrous composition.

14. The anhydrous composition of claim 1, wherein the NO-releasing compound is present in the anhydrous composition at a concentration of about 20% by weight of the anhydrous composition.

15. The anhydrous composition of claim 1, wherein the NO-releasing compound is present in the anhydrous composition at a concentration of about 24% by weight of the anhydrous composition.

16. The anhydrous composition of claim 1, wherein the NO-releasing compound is present in the anhydrous composition at a concentration of about 30% by weight of the anhydrous composition.

17. The anhydrous composition of claim 1, wherein the NO-releasing compound is present in the anhydrous composition at a concentration of about 32% by weight of the anhydrous composition.

18. The anhydrous composition of claim 1, wherein the NO-releasing compound comprises diazeniumdiolated co-condensed silica particles.

* * * * *

UNITED STATES PATENT AND TRADEMARK OFFICE
CERTIFICATE OF CORRECTION

PATENT NO. : 10,265,334 B2
APPLICATION NO. : 14/887648
DATED : April 23, 2019
INVENTOR(S) : Doxey et al.

Page 1 of 1

It is certified that error appears in the above-identified patent and that said Letters Patent is hereby corrected as shown below:

In the Specification

Column 1, Lines 5-9: Please replace the entire paragraph, under the heading "RELATED APPLICATION DATA", with the following paragraph:
This application is a continuation of United States Patent Application No. 14/134,737, filed December 19, 2013, which is a continuation under 35 U.S.C. § 111(a) of International Application No. PCT/US2012/045384, filed on July 3, 2012, which claims the benefit, under 35 U.S.C. § 119, of U.S. Provisional Application No. 61/504,628, filed July 5, 2011 and U.S. Provisional Application No. 61/610,137, filed March 13, 2012, the disclosures of each of which are incorporated herein by reference in their entirety.

Signed and Sealed this
Thirtieth Day of July, 2019

Andrei Iancu
*Director of the United States Patent and Trademark Office*